United States Patent
Duggal et al.

(10) Patent No.: US 9,119,678 B2
(45) Date of Patent: Sep. 1, 2015

(54) FACET FIXATION SYSTEMS

(71) Applicants: Neil Duggal, London (CA); Dylan M. Hushka, Gilbert, AZ (US); Joshua A. Butters, Chandler, AZ (US); Nicholas Slater, Chandler, AZ (US)

(72) Inventors: Neil Duggal, London (CA); Dylan M. Hushka, Gilbert, AZ (US); Joshua A. Butters, Chandler, AZ (US); Nicholas Slater, Chandler, AZ (US)

(73) Assignee: SYNERGY DISC REPLACEMENT INC., Kitchener (CA)

( * ) Notice: Subject to any disclaimer, the term of this patent is extended or adjusted under 35 U.S.C. 154(b) by 2 days.

(21) Appl. No.: 13/662,993

(22) Filed: Oct. 29, 2012

(65) Prior Publication Data

US 2013/0123848 A1 May 16, 2013

Related U.S. Application Data

(63) Continuation-in-part of application No. 13/367,308, filed on Feb. 6, 2012.

(60) Provisional application No. 61/554,218, filed on Nov. 1, 2011, provisional application No. 61/672,093, filed on Jul. 16, 2012.

(51) Int. Cl.
*A61B 17/86* (2006.01)
*A61B 17/70* (2006.01)

(52) U.S. Cl.
CPC .......... *A61B 17/7064* (2013.01); *A61B 17/8695* (2013.01)

(58) Field of Classification Search
CPC ............. A61B 17/683; A61B 17/8695; A61B 17/7064
See application file for complete search history.

(56) References Cited

U.S. PATENT DOCUMENTS

| | | | |
|---|---|---|---|
| 2,489,870 A * | 11/1949 | Dzus | 606/310 |
| 4,011,602 A | 3/1977 | Rybicki et al. | |
| 4,263,904 A | 4/1981 | Judet | |
| 4,590,928 A | 5/1986 | Hunt et al. | |
| 4,858,603 A | 8/1989 | Clemow et al. | |
| 4,878,794 A | 11/1989 | Potucek | |
| 4,898,186 A | 2/1990 | Ikada et al. | |
| 5,108,395 A * | 4/1992 | Laurain | 606/86 B |
| 5,487,744 A | 1/1996 | Howland | |
| D368,777 S | 4/1996 | Goble et al. | |

(Continued)

FOREIGN PATENT DOCUMENTS

| WO | WO2011040986 | 4/2011 |
|---|---|---|
| WO | WO2012009162 | 1/2012 |

OTHER PUBLICATIONS

Orthopedics; Interfacet Distance and Facet Arthrosis: Dec. 2009 vol. 32 . No. 12.

(Continued)

*Primary Examiner* — David Bates
*Assistant Examiner* — Samuel Hanna
(74) *Attorney, Agent, or Firm* — Maywood IP Law; Barbara Daniels; David Meibos

(57) ABSTRACT

Facet fixation implants include a cap member with a circular base portion and an eccentric raised portion. The raised portion includes first and second lobes and is smoothly contoured to provide an unobtrusive profile when implanted. Beveled teeth project from the implant to provide fixation and compression across the facet joint. The cap member includes an offset aperture which receives a fastener. Tools, guiding instruments and methods for implantation of the implants are disclosed.

13 Claims, 30 Drawing Sheets

(56) References Cited

U.S. PATENT DOCUMENTS

| | | | |
|---|---|---|---|
| D374,286 S | 10/1996 | Goble et al. | |
| D374,287 S | 10/1996 | Goble et al. | |
| D374,482 S | 10/1996 | Goble et al. | |
| 5,681,311 A | 10/1997 | Foley et al. | |
| 6,123,711 A | 9/2000 | Winters | |
| 6,248,108 B1 | 6/2001 | Törmälä et al. | |
| 6,280,443 B1 | 8/2001 | Gu et al. | |
| 6,610,091 B1 | 8/2003 | Riley | |
| 6,648,893 B2 | 11/2003 | Dudasik | |
| 6,723,095 B2 | 4/2004 | Hammerslag | |
| 6,808,526 B1 | 10/2004 | Magerl et al. | |
| 6,811,567 B2 | 11/2004 | Reiley et al. | |
| 6,923,814 B1 | 8/2005 | Hildebrand et al. | |
| 6,945,975 B2 | 9/2005 | Dalton | |
| 6,979,333 B2 | 12/2005 | Hammerslag | |
| 7,090,675 B2 | 8/2006 | Songer et al. | |
| 7,101,398 B2 | 9/2006 | Dooris et al. | |
| 7,563,275 B2 | 7/2009 | Falahee | |
| 7,608,094 B2 | 10/2009 | Falahee | |
| 7,699,878 B2 | 4/2010 | Pavlov et al. | |
| 7,708,761 B2 | 5/2010 | Petersen | |
| 7,744,630 B2 | 6/2010 | Lancial | |
| 7,749,251 B2 | 7/2010 | Obenchain | |
| 7,799,057 B2 | 9/2010 | Hudgins et al. | |
| 7,837,713 B2 | 11/2010 | Petersen | |
| 7,909,826 B2 | 3/2011 | Serhan et al. | |
| 8,002,799 B2 | 8/2011 | Chin et al. | |
| 8,043,343 B2 | 10/2011 | Miller et al. | |
| 8,585,744 B2 * | 11/2013 | Duggal et al. | 606/301 |
| 2005/0192580 A1 | 9/2005 | Dalton | |
| 2005/0197700 A1 | 9/2005 | Boehm | |
| 2005/0240188 A1 | 10/2005 | Chow et al. | |
| 2006/0064099 A1 | 3/2006 | Pavlov et al. | |
| 2006/0190081 A1 | 8/2006 | Kraus et al. | |
| 2006/0217715 A1 * | 9/2006 | Serhan et al. | 606/61 |
| 2006/0293663 A1 * | 12/2006 | Walkenhorst et al. | 606/61 |
| 2007/0250166 A1 | 10/2007 | McKay | |
| 2008/0177334 A1 | 7/2008 | Stinnette | |
| 2008/0234758 A1 | 9/2008 | Fisher et al. | |
| 2008/0255622 A1 | 10/2008 | Mickiewicz et al. | |
| 2008/0255666 A1 | 10/2008 | Fisher et al. | |
| 2009/0036927 A1 | 2/2009 | Vestgaarden | |
| 2009/0082875 A1 * | 3/2009 | Long | 623/21.18 |
| 2009/0192551 A1 | 7/2009 | Cianfrani et al. | |
| 2009/0312763 A1 | 12/2009 | McCormack et al. | |
| 2009/0312800 A1 | 12/2009 | Chin et al. | |
| 2010/0069965 A1 | 3/2010 | Abdou | |
| 2010/0094356 A1 | 4/2010 | Varela et al. | |
| 2010/0280555 A1 | 11/2010 | Aflatoon et al. | |
| 2011/0182693 A1 | 7/2011 | Helgerson et al. | |
| 2011/0190821 A1 | 8/2011 | Chin | |
| 2011/0245877 A1 * | 10/2011 | Pisharodi | 606/268 |
| 2012/0010662 A1 * | 1/2012 | O'Neil et al. | 606/279 |
| 2012/0010669 A1 | 1/2012 | O'Neil et al. | |
| 2012/0116454 A1 | 5/2012 | Edidin et al. | |

OTHER PUBLICATIONS

Medco Forum; Percutaneous Lubmar Fixation Via Perpos PLS System From Interventional Spine: vol. 15 No. 37 Sep. 2008.

Medco Forum; Percutaneous Lumbar Fixation via Perpos PLS System from Interventional Spine: vol. 16 No. 37 Oct. 2009.

Interventional Spine; Bone Lock: Product Brochure, 2009 PN 7320 Rev. C DCR 837.

Concero; Facet Screw System Website WWW.lanx.com Jun. 30, 2011 @ 8:09 am MT.

Chin, Kingsley R; Early Results of the Triage Medical Percutaneous Transfacet Pedicular Bone-Lok Compression Device for Lumbar Fusion: 5008 Rev. B, DCR 628.

SpineFrontier; FacetFuse, Chameleon MIS Screw System; Website, www.spinefrontier.com.

Medco Forum; Perpos PLS System from Interventional Spine, vol. 16, No. 61 Nov. 2009.

Mahar, Andrew; Journal of Spinal Disorders Technology: Biomechanical Comparison of a Novel Percutaneous Transfacet Device and a Traditional Posterior System for Single ;Level Fusion, vol. 19, No. 8, Dec. 2006.

Amedica; Javelin: MIS Locking Facet System, www.amedica.com Oct. 21, 2011 @ 3:05 pm MT.

Life Spine; FS3 Facet Screw Spinal System: www.lifespine.com Jun. 21, 2011 @ 12:18 pm MT.

Trans1; Lumbar Fusion Vectre; www.trans1.com Jun. 27, 2011 @ 10:03 am MT.

Amendia; Spartan Facet Screw www.amendia.com May 24, 2012 @ 9:17 am.

Spineology; Capture Facet Screw: Apr. 2010 Rev. F.

US Spine; Facet Bolt Design: www.us-spine.com.

X-spine Systems, Inc; Fixcet: www.x-spine.com Jun. 30, 2011 @ 8:32 am.

Globus Medical; Zyfuse: www.globusmedical.com Jun. 30, 2011 9:23 am MT.

* cited by examiner

FACET FIXATION SYSTEMS

CROSS-REFERENCE TO RELATED APPLICATIONS

This application is a continuation-in-part of:
U.S. patent application Ser. No. 13/367,308, filed Feb. 6, 2012 and entitled JOINT AND BONE FIXATION.
This application is also a non-provisional of:
U.S. Provisional Patent Application No. 61/554,218, filed Nov. 1, 2011 and entitled SYSTEMS AND METHODS FOR FACET FIXATION.
This application is also a non-provisional of:
U.S. Provisional Patent Application No. 61/672,093, filed Jul. 16, 2012 and entitled FACET FIXATION SYSTEMS.
The above-identified documents are herein incorporated by reference in their entirety.

BACKGROUND OF THE DISCLOSURE

The present disclosure relates to bone and joint fixation and instrumentation and methods for preparation and implantation of these devices. Joint fixation may be necessary in cases of pain and inflammation due to cartilage degeneration, nerve impingement, spinal misalignment, and motion instability. The primary examples described herein illustrate how this concept is applied to the facet joint, but this concept applies equally to other joints where similar causes of pain and inflammation are indicated.

Facet fixation devices are typically implanted as a minimally invasive means of posteriorly stabilizing the spine. Biomechanical studies have shown that facet screw systems perform similarly or better than pedicle screw systems. Many commercially available facet screws require a complex and timely oblique fluoroscopic technique to achieve the proper placement trajectory. The facet fixation system disclosed herein employs a simple pedicle targeting trajectory requiring only M/L and A/P fluoroscopy. The cap geometry reduces placement sensitivity and allows the surgeon to capture and compress an increased bone surface, while optionally lateralizing the implant to better accommodate interspinous process access.

Those of skill in the art will recognize that the following description is merely illustrative of the principles of the disclosure, which may be applied in various ways to provide many different alternative embodiments and may be applicable outside the fields of surgery or medical devices. While the present disclosure is made in the context of facet joints in the lumbar spinal region for the purposes of illustrating the concepts of the design, it is contemplated that the present design and/or variations thereof may be suited to other uses, such as cervical facet joints, thoracic facet joints, other joints in the human body, or to stabilize bone fractures, etc. Moreover, the implants, instrumentation and methods set forth herein may be used in open, percutaneous, and/or minimally invasive procedures and may be placed via intra-facet, trans-facet, trans-laminar, or trans-pedicle means.

All changes which come within the meaning and range of equivalency of the claims are to be embraced within their scope.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

SUMMARY OF THE DISCLOSURE

In an embodiment, a device for facet joint fixation comprises a fastener and a cap, the cap including: a base portion having a circular perimeter; a raised portion protruding from the base portion, the raised portion having a non-circular perimeter, the raised portion including a first lobe and a second lobe, the first lobe wider than the second lobe; and an aperture extending through the base portion and the raised portion, the aperture shaped to receive the fastener to allow the fastener to fasten the cap to a facet joint to stabilize the facet joint.

BRIEF DESCRIPTION OF THE DRAWINGS

Various embodiments of the present disclosure will now be discussed with reference to the appended drawings. It will be appreciated that these drawings depict only typical examples of the present disclosure and are therefore not to be considered limiting of its scope.

DETAILED DESCRIPTION

While certain embodiments are shown and described in detail below by way of illustration only, it will be clear to the person skilled in the art upon reading and understanding this disclosure that changes, modifications, and variations may be made and remain within the scope of the technology described herein. Furthermore, while various features are grouped together in the embodiments for the purpose of streamlining the disclosure, it is appreciated that features from different embodiments may be combined to form additional embodiments which are all contemplated within the scope of the disclosed technology.

Not every feature of each embodiment is labeled in every figure in which that embodiment appears, in order to keep the figures clear. Similar reference numbers (for example, those that are identical except for the first numeral) may be used to indicate similar features in different embodiments.

Any of the devices described herein may be fabricated from metals, alloys, polymers, plastics, ceramics, glasses, composite materials, or combinations thereof, including but not limited to: PEEK (polyether ether ketone), titanium, titanium alloys, commercially pure titanium grade 2, ASTM F67, Nitinol, cobalt chrome, stainless steel, UHMWPE (ultra-high molecular-weight polyethylene) and biodegradable materials, among others. Different materials may be used within a single part. The implants disclosed herein may also encompass a variety of surface treatments or additives to encourage bony attachment, including but not limited to: porous coatings, hydroxyapatite, TCP (tricalcium phosphate), anti-microbial additives, analgesics, anti-inflammatories, BMPs (bone morphogenic proteins), PMA (phorbol myristate acetate) material, bone growth promoting material, PLLA (poly-L-lactide), PGA (polyglycolide), TCP (tricalcium phosphate), demineralized bone, cancellous bone chips, etc. Any implant disclosed herein may include a radiographic marker for imaging purposes. Any implant disclosed herein may be colored, coded or otherwise marked to make it easier for the surgeon to identify the type and size of the implant.

Figure 1A:
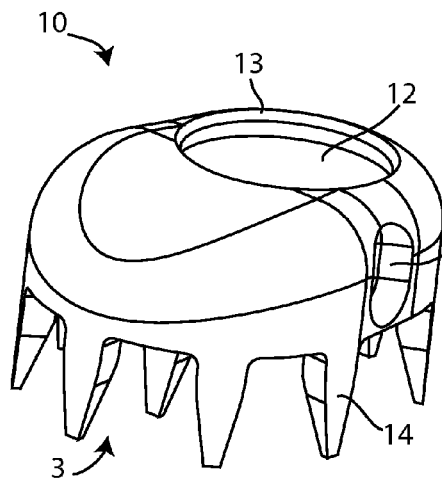
FIG. 1A is an isometric view of a cap in accordance with one example of the present disclosure.
Figure 1B:
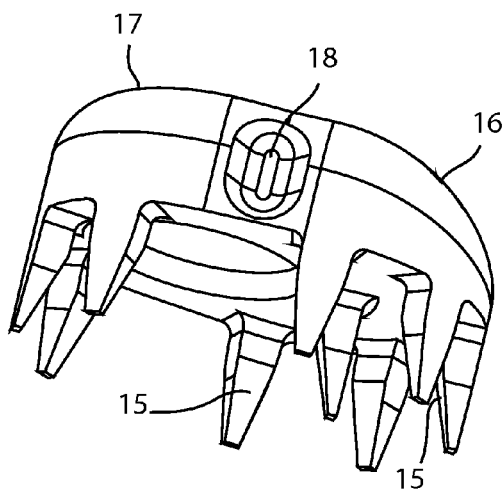
FIG. 1B is a bottom isometric view of the cap in FIG. 1A.
Figure 1C:
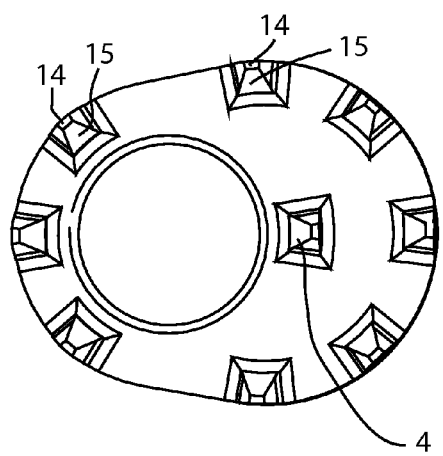
FIG. 1C is a bottom view of the cap in FIG. 1A.
Figure 1D:
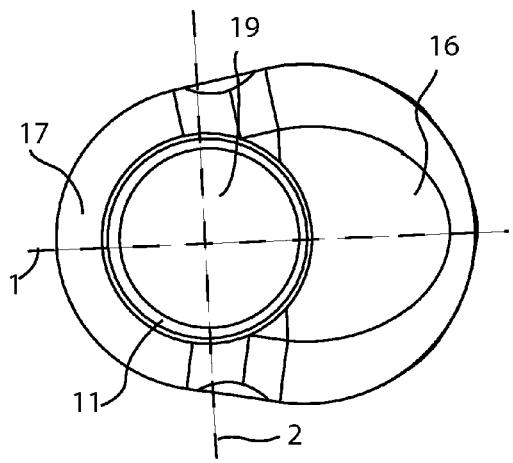
FIG. 1D is a top view of the cap in FIG. 1A.
Figure 1E:
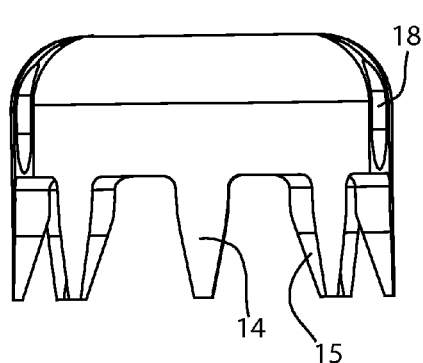
FIG. 1E is a back view of the cap in FIG. 1A.
Figure 1F:
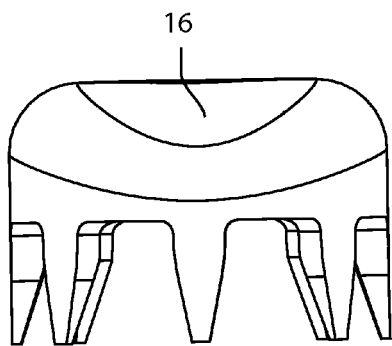
FIG. 1F is a front view of the cap in FIG. 1A.
Figure 1G:
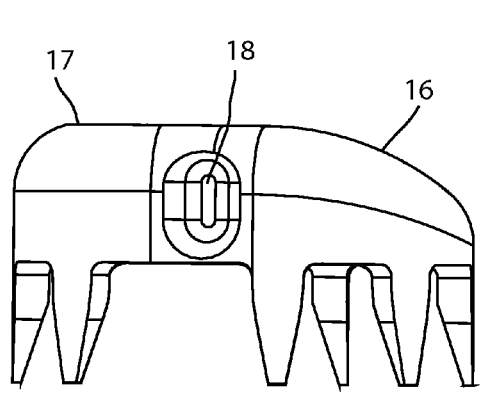
FIG. 1G is a left side view of the cap in FIG. 1A.
Figure 1H:
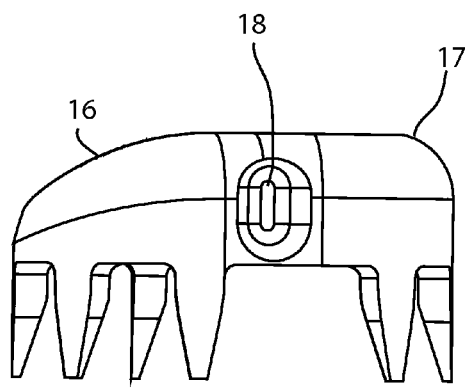
FIG. 1H is a right side view of the cap in FIG. 1A.
Figure 2A:
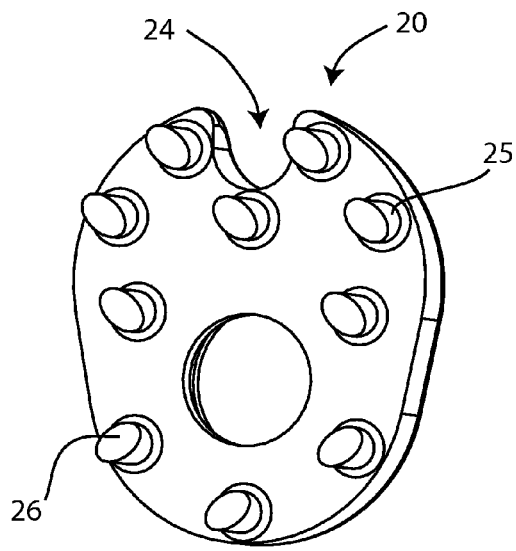
FIG. 2A is an isometric view of a cap in accordance with another example of the present disclosure.
Figure 2B:
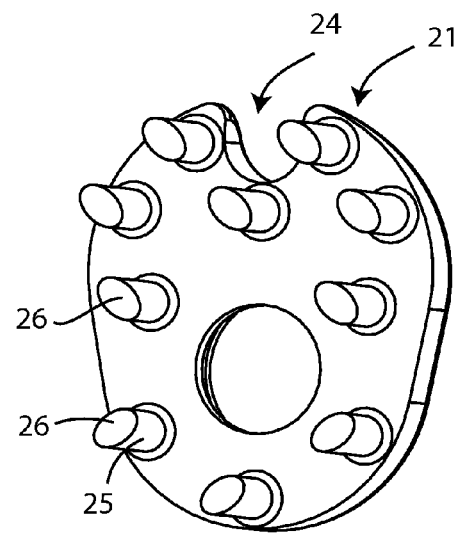
FIG. 2B is an isometric view of the cap in FIG. 2A with longer teeth.
Figure 2C:
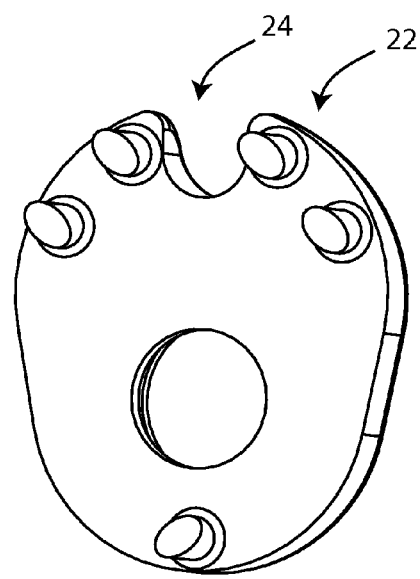
FIG. 2C is an isometric view of a cap in accordance with another example of the present disclosure.
Figure 2D:
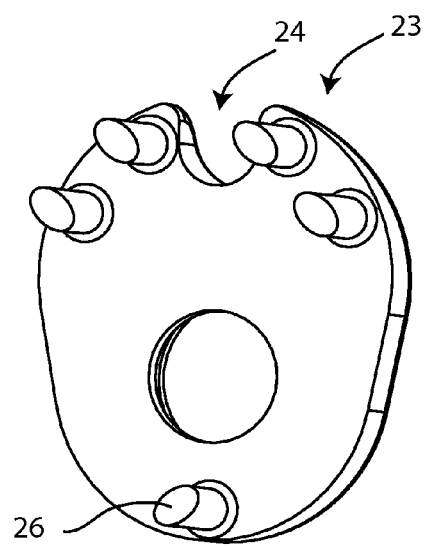
FIG. 2D is an isometric view of the cap of FIG. 2C with longer teeth.

FIGS. 1A-1H illustrate one example of a cap member useful for fixing a bone fracture or joint to provide stabilization. The cap members disclosed herein may be referred to as caps or washers. The cap 10 can have a first portion 16 and a second portion 17. Referring to FIG. 1D, the first portion 16 can be longer than the second portion 17 along a first axis 1 which intersects the first portion, the second portion, and an aperture 19 formed in the cap 10. In some examples, the first portion 16 may also be longer then the second portion 17 along a second axis 2. This creates an eccentrically shaped cap 10 with the first portion 16 being asymmetrically shaped in comparison to the second portion 17. The shape of the cap 10 can also be referred to as "oblong" in some examples, with the first portion 16 forming a lobe that is larger than the second portion 17. The eccentric shape of the cap 10 allows a surgeon more freedom to orient the larger lobe portion across the joint to facilitate joint fixation and increases the load bearing area of the implant 10. In some examples, the cap 10 can also curve downward to create a lower profile implant. For example, FIGS. 1G and 1H show left and right side views of the cap 10 with the first portion 16 of the cap curving downward.

The cap 10 can include one or more teeth 14 on a bone engaging side 3 of the cap 10. The plurality of teeth 14 can have beveled surfaces 15 that are arranged to at least partially oppose each other between the first portion 16 of the cap 10 and the second portion 17 of the cap 10. The beveled surfaces 15 can be made to diverge away from each other in the superior to inferior direction and converge toward each other in the inferior to superior direction. In this manner, the beveled surfaces 15 can act to compress the joint bones together as the teeth 14 are driven into the bones. The angle of the beveled services 15 can be adjusted to increase or decrease the compressive forces created by the cap 10. For example, if the angle of the beveled surfaces 15 is increased, the teeth can impart a greater compressive force for a given distance that the teeth 14 are driven into the bones. Thus, the size, length, bevel shape, bevel angle, and distribution of the teeth may vary in any of the examples disclosed herein. For example, the number and spacing of the teeth 14 can be chosen to maximize the fixation properties of the cap 10 in view of the size and condition of the joint bones of the patient. In some examples, the teeth 14 can be distributed on the bone engaging side 3 of the cap 10 along the outer perimeter of the bone engaging side 3 of the cap 10. In other examples the teeth 14 can be distributed away from the outer perimeter of the bone engaging side 3 of the cap 10. For example, FIG. 1C has a tooth 4 which does not lie along the outer perimeter of the bone engaging side 3 of the cap 10, rather tooth 4 is located deeper within the interior of the first portion 16. Having teeth distributed in this manner can increase the bone grabbing performance of the implant by increasing the number of teeth within the interior of the first portion 16.

Figure 5A:
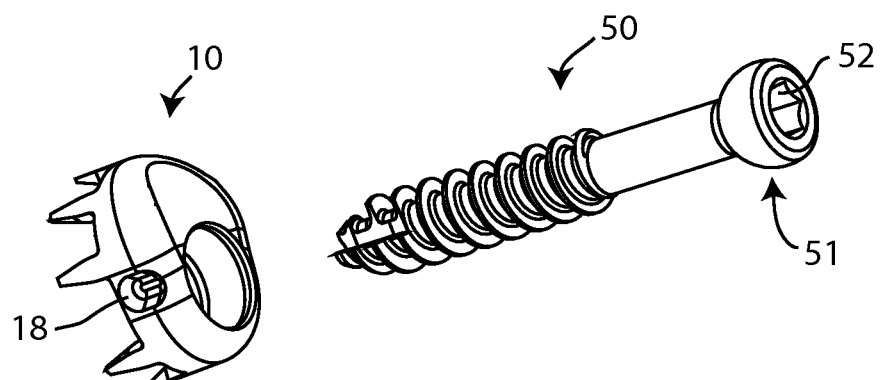
FIG. 5A shows an implant comprising the cap of FIG. 1A and a fastener before they are assembled together.
Figure 5B:
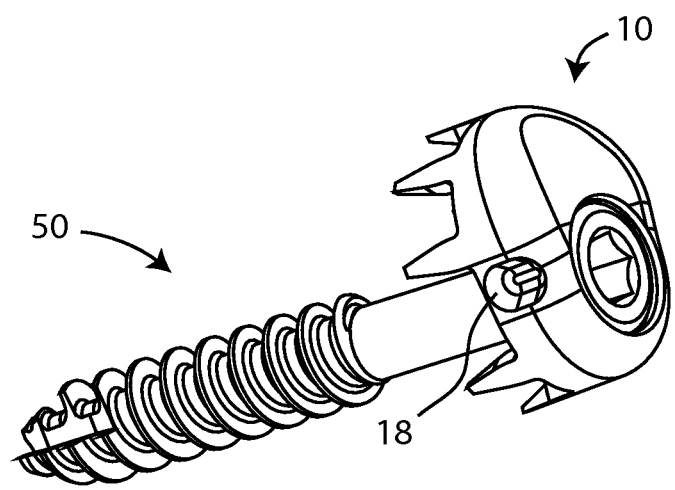
FIG. 5B shows the cap of FIG. 1A and the fastener of FIG. 5A after they are assembled together.

Continuing with FIGS. 1A and 1D, the cap 10 can have an aperture 19 formed through the cap 10 and configured to receive a suitable fastener 50, as can be seen in FIGS. 5A-5B. The shaft of the fastener 50 may be partially threaded to promote compression. The fastener 50 can also be self-tapping (or self-threading) and may be cannulated down its center so that it can be placed into the facet joint with a K-wire. The cap 10 can have a chamfered spherical capsule 12 shaped to receive a complimentarily shaped partially spherical fastener head 51, as shown in FIG. 5A. This allows the fastener 50 to rotate within the aperture 19 and concentrically pivot along its longitudinal axis to ensure that the cap 10 can align itself with the joint bones as the cap 10 is forced into the joint bones. The aperture 19 can also be deep enough to allow the fastener head 51 to be recessed within the aperture 19 to provide a smooth, low profile implant. A smooth, low profile implant can help reduce irritation to surrounding soft tissue. The aperture 19 may also be encircled by a lip 13 which projects inward and has a diameter slightly smaller in size than the diameter of the head portion 51 of the suitable fastener 50. This can allow the fastener to be "press fit" into the aperture such that the lip 13 provides an interference that captures the fastener 50 within the aperture 19. The lip 13 can be flush with the surrounding surface of the implant to avoid any abrupt changes in the shape of the implant resulting in smooth surfaces. Thus, the smooth lip 13 that sits flush with the surrounding surface will help reduce irritation to surrounding soft tissues, as compared to other interference fit configurations, such as collet style interference structures which have multiple slits and protruding structures that can cause interference and irritation to surrounding soft tissues and bones.

Figure 3:
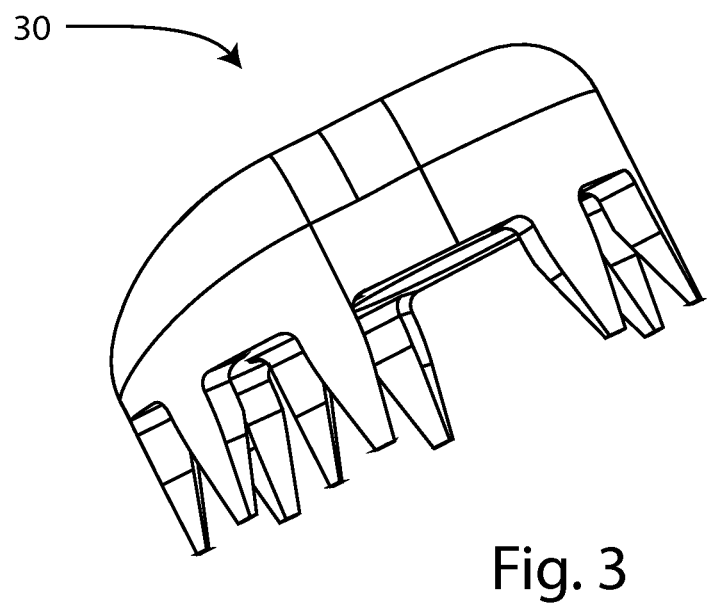
FIG. 3 is an isometric view of a cap in accordance with another example of the present disclosure.

Continuing with FIGS. 1A-1H, the cap 10 can have one or more recessed slots 18 formed in a surface of the cap 10. The slots 18 can interact with a guide tool to hold the cap 10 in a specific orientation during insertion. In other examples, the cap 10 may not include one or more slots 18 formed in a surface of the cap 10. One such example can be seen in FIG. 3.

FIGS. 2A-2D illustrate alternative examples of caps 20, 21, 22, and 23 which can be used to fix bones or joints according to other examples of the present disclosure. Each of the caps 20, 21, 22, and 23 may include one or more slots 24 configured to interact with a guide tool to hold the cap at a specific orientation during insertion. However, in other examples, the cap may not include one or more slots 24. It will be appreciated that the location of the one or more slots 24 around the perimeter of the caps may vary, as may the size, diameter and/or number of the one or more slots 24. The one or more slots 24 may cooperate with a suitable guide for properly aligned placement of the cap into the joint, as will be discussed in greater detail below. The caps 20, 21, 22, and 23 can also include a plurality of teeth 25 that can be cylindrical in shape and have varying lengths. The teeth 25 can also include opposing beveled surfaces 26 similar to other embodiments disclosed herein.

Figure 4:
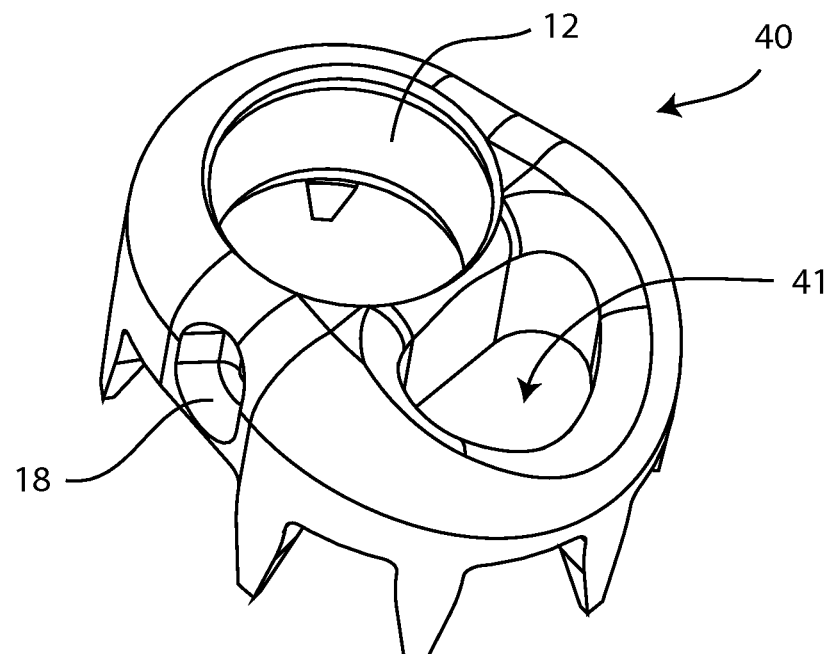
FIG. 4 is an isometric view of a cap in accordance with another example the present disclosure.
Figure 6:
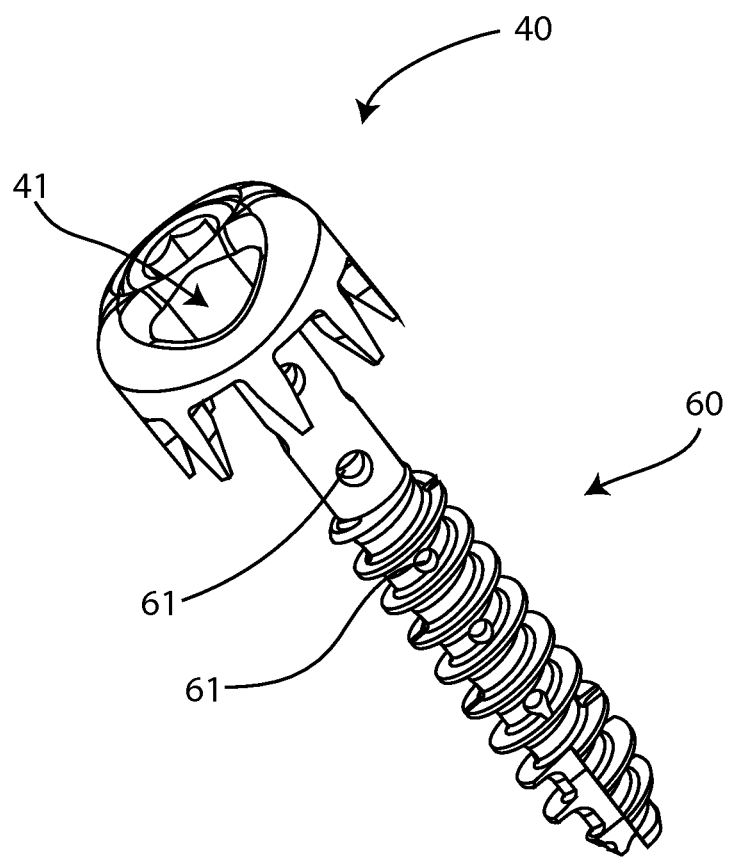
FIG. 6 shows a cap and fastener assembly according to another example of the present disclosure.

Referring now to FIG. 4, a cap 40 is shown with an aperture or fenestration 41 formed through the cap 40 and configured to promote bone growth, or bone fusion, by providing a graft pocket for material such as bone chips or bone growth promoters. FIG. 6 illustrates the cap 40 in combination with a faster 60, which is also fenestrated with apertures 61 throughout the fastener 60 which can also be packed with bone chips or bone growth promoters. This combination may further promote bony ingrowth and bone fusion between the faster 60, the cap 40, and the bones.

Figure 7A:
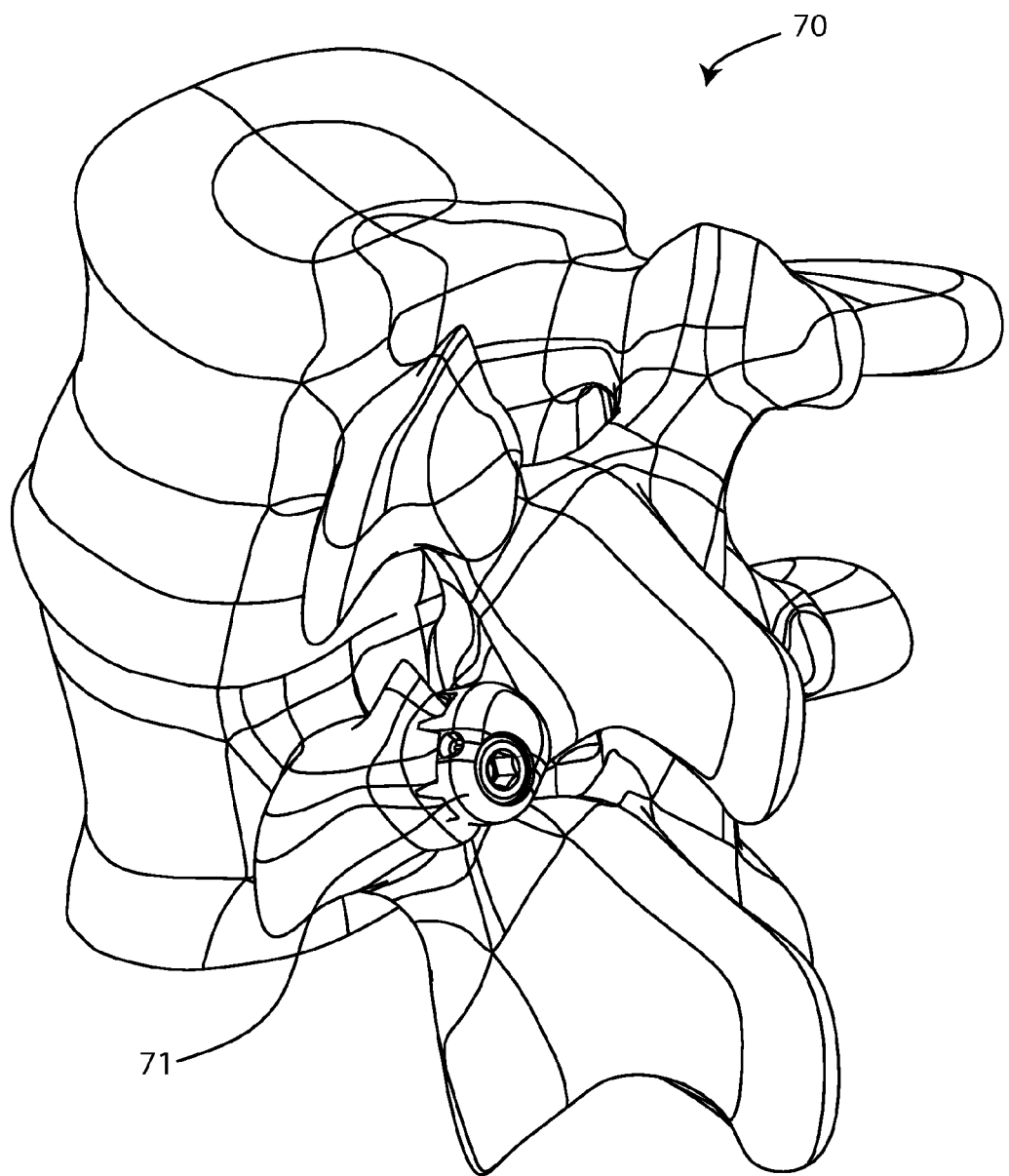
FIG. 7A shows a portion of a spine with an implant fastened to a facet joint according to the present disclosure.
Figure 7B:
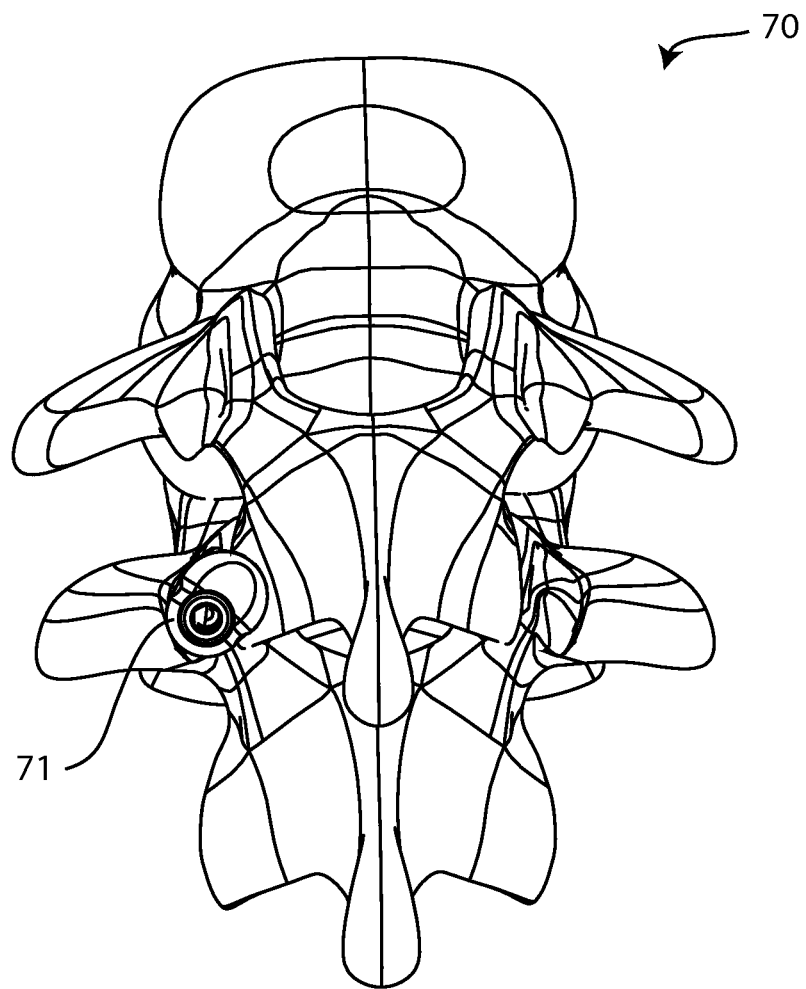
FIG. 7B shows a back isometric view of the spine and implant of FIG. 7A.
Figure 8A:
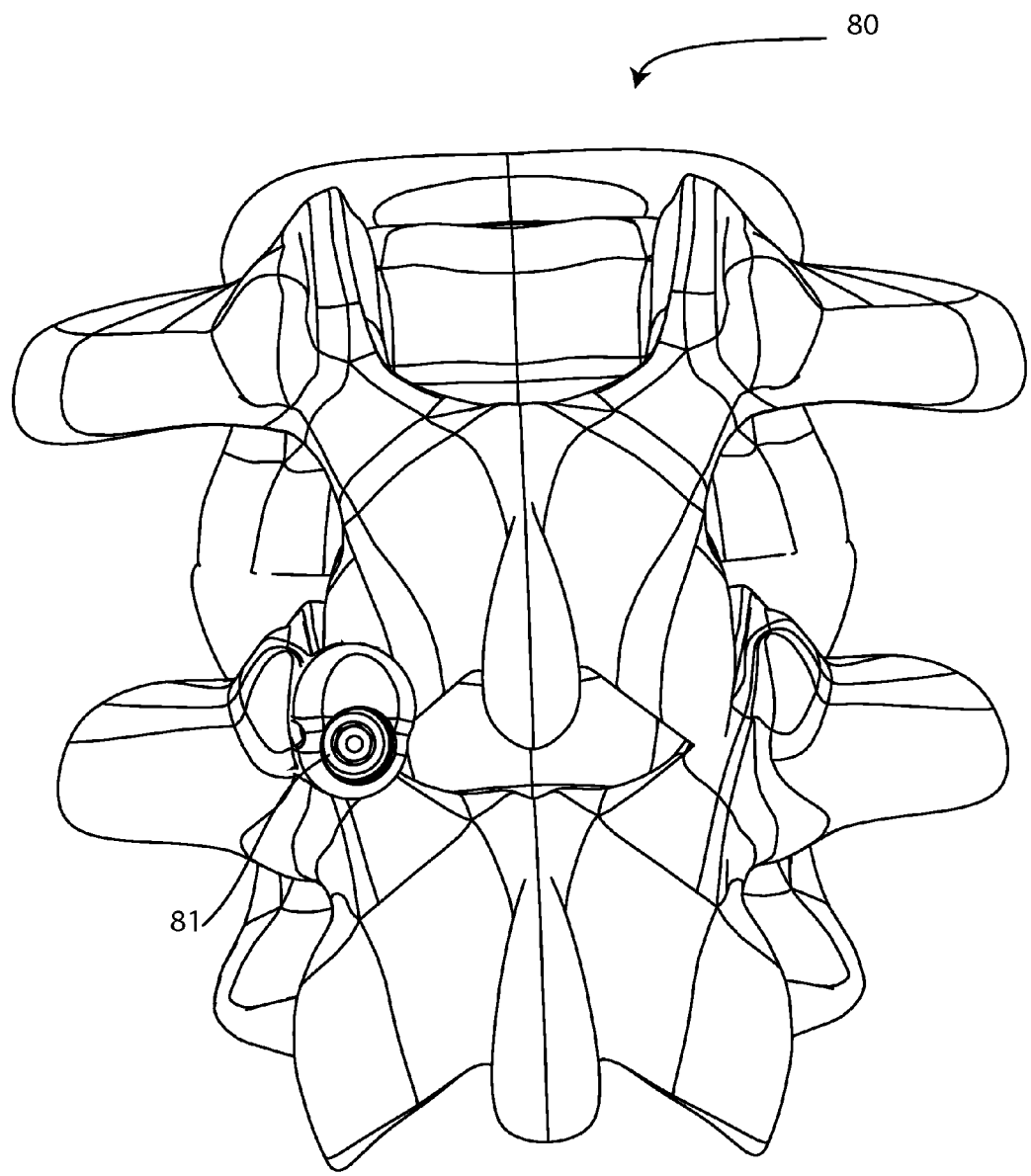
FIG. 8A shows an isometric view of a portion of a spine with an implant fastened to a facet joint in a first orientation.
Figure 8B:
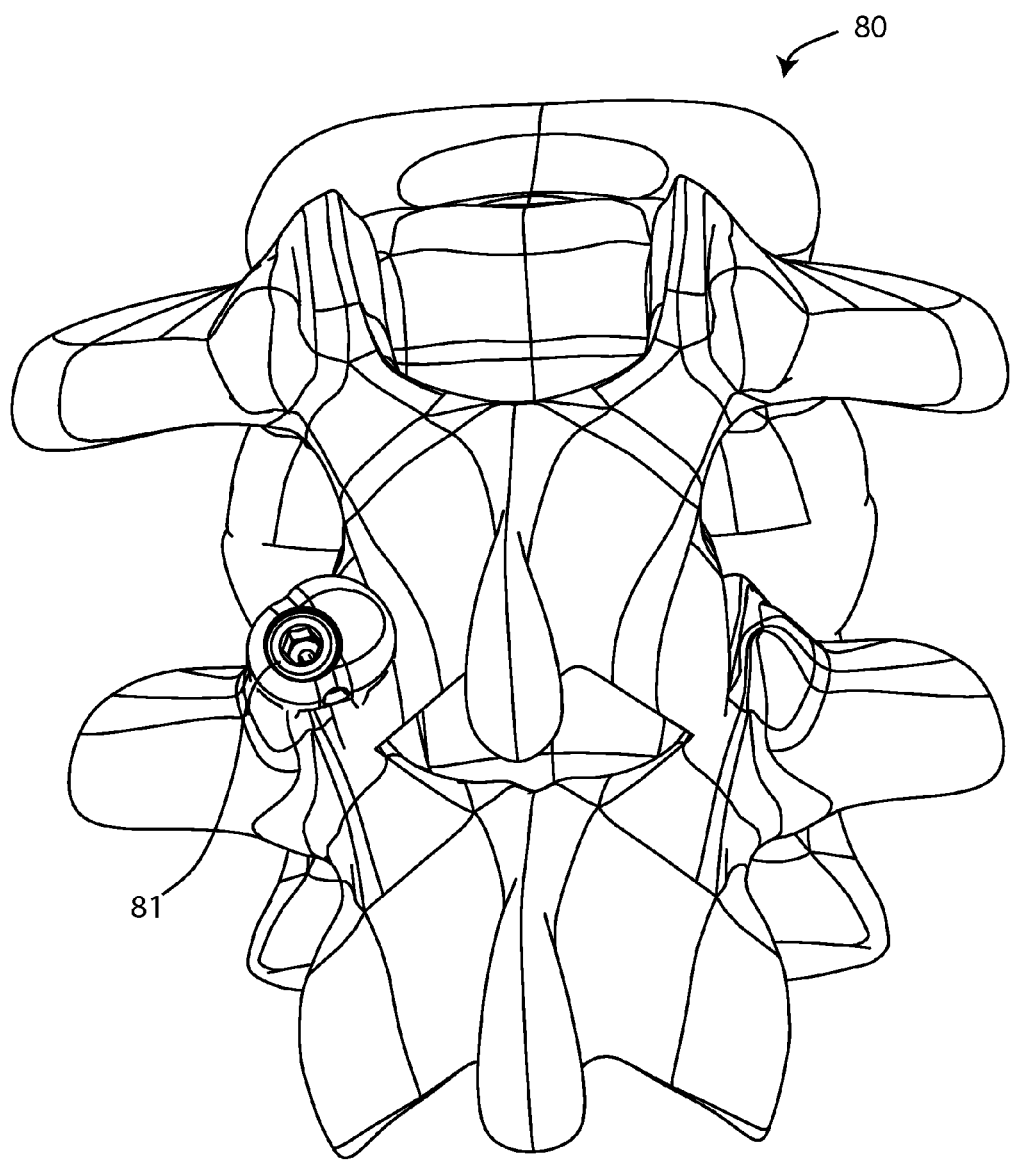
FIG. 8B shows an isometric view of a portion of a spine with an implant fastened to a facet joint in a second orientation.
Figure 8C:
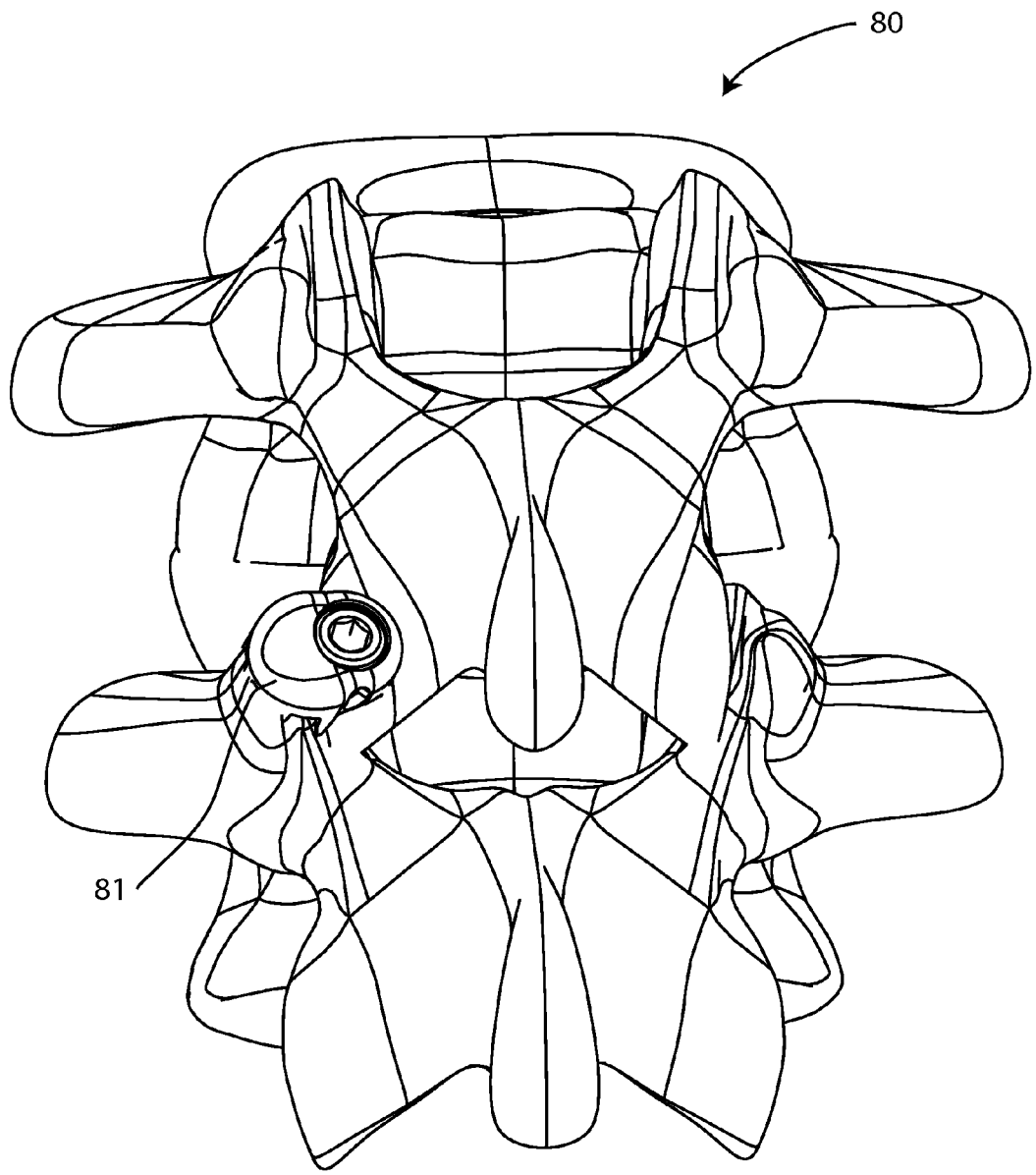
FIG. 8C shows an isometric view of a portion of a spine with an implant fastened to a facet joint in a third orientation.
Figure 8D:
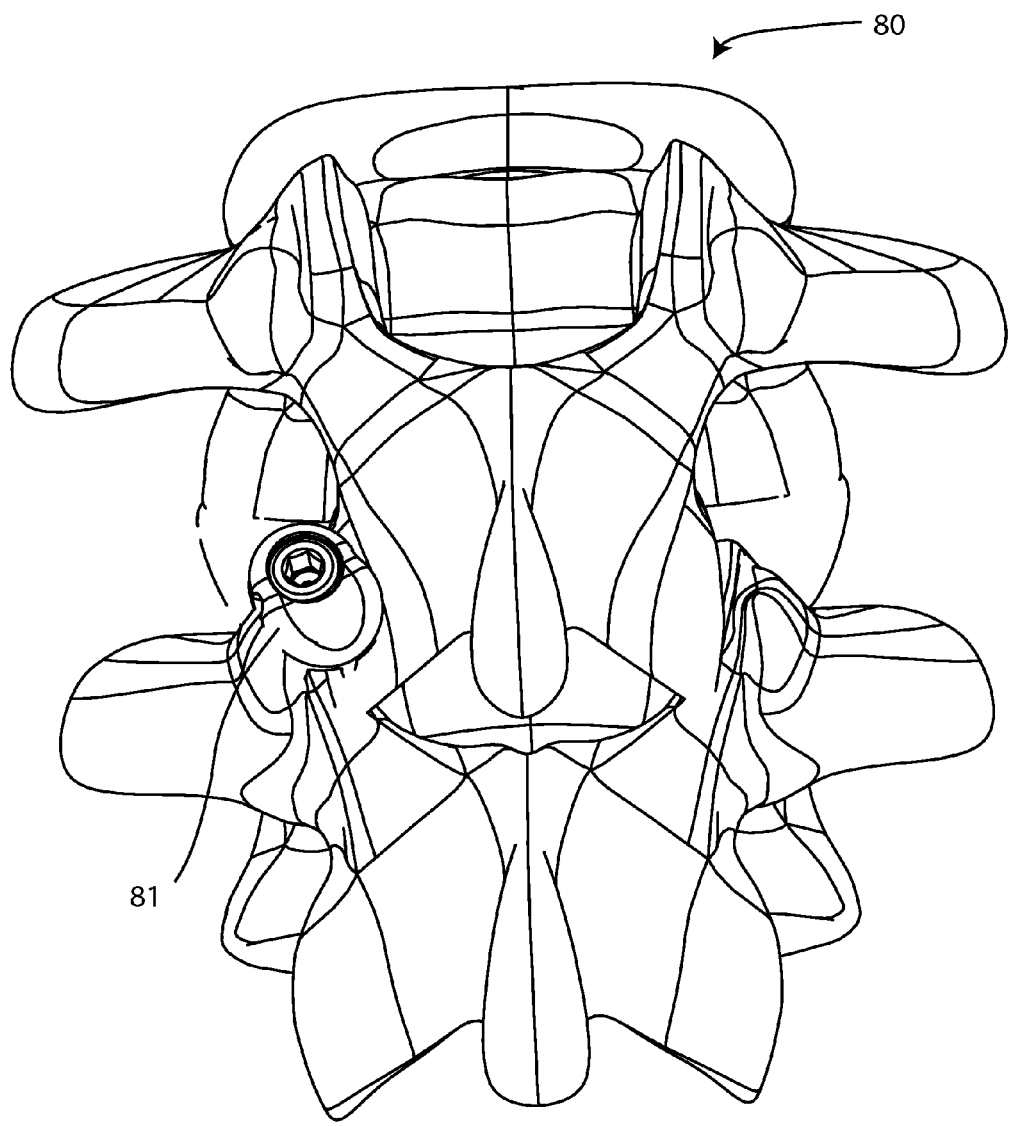
FIG. 8D shows an isometric view of a portion of a spine with an implant fastened to a facet joint in a fourth orientation.
Figure 8E:
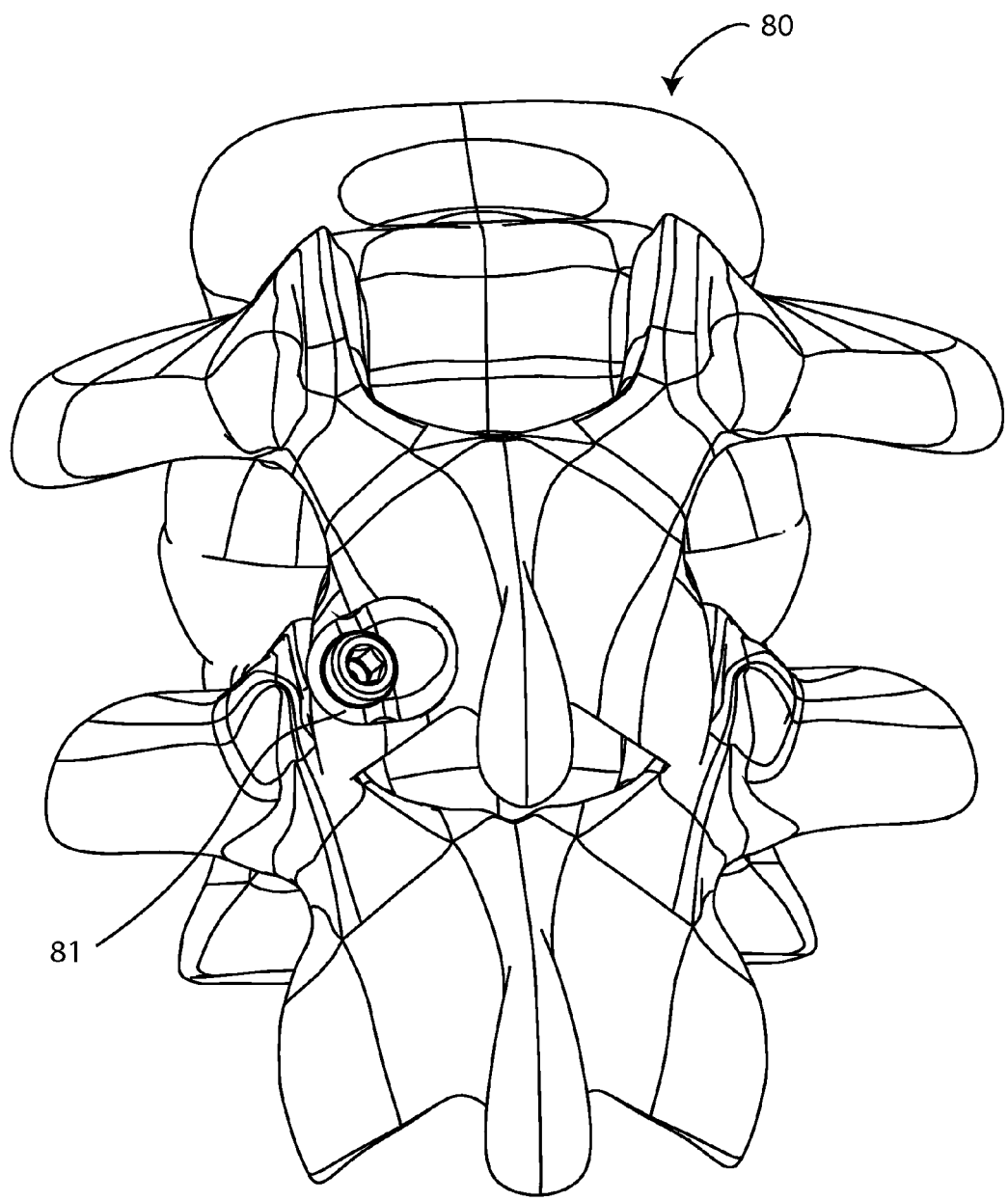
FIG. 8E shows an isometric view of a portion of a spine with an implant fastened to a facet joint in a fifth orientation.
Figure 9:
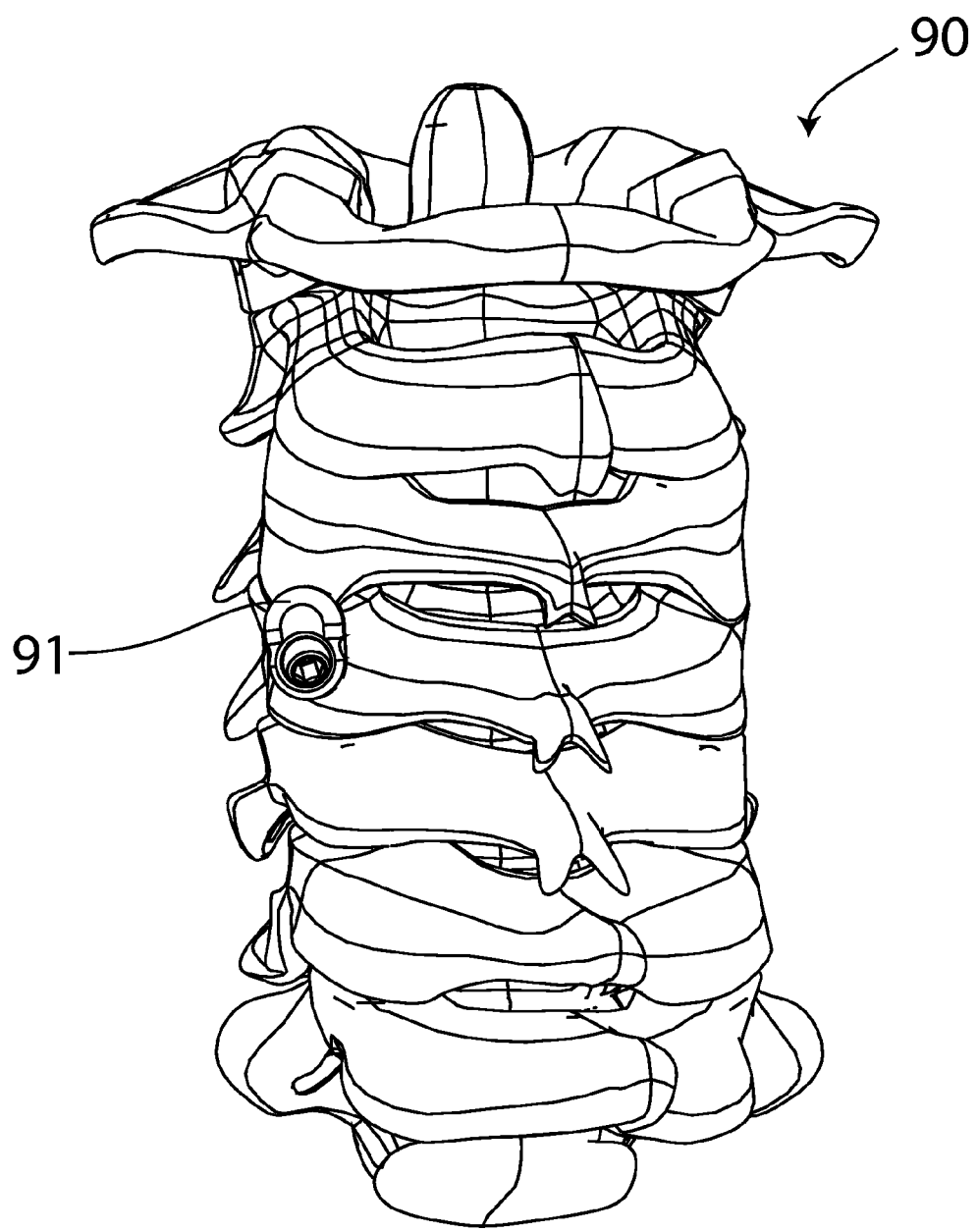
FIG. 9 shows a portion of a cervical spine with an implant fastened to a facet joint according to the present disclosure.

FIGS. 7-9 show various implants affixed to facet joints in portions of the spine. FIG. 7A shows an isometric view of an implant 71 affixed to a facet joint in a lumbar portion of a spine 70. FIG. 7A shows a back isometric view of the implant 71 affixed to the lumbar portion of the spine 70 in FIG. 7.

FIGS. 8A-8E show examples of various placement options for an implant 81 in a portion of a spine 80, all of which are easily achievable with the guides and instrumentation disclosed herein. FIG. 8A shows the cap 81 with the fastener piercing the lower or inferior part of the superior articular process and the lobe of the cap oriented superiorly to capture the inferior articular process with the lobe of the cap 81. FIG. 8B shows the cap 81 with the fastener piercing the lateral or middle part of the superior articular process and the lobe of the cap oriented medially to capture the inferior articular process with the lobe of the cap 81. FIG. 8C shows the cap 81 with the fastener piercing the inferior articular process (transfacet) and the lobe of the cap is inverted or oriented laterally to capture the superior articular process with the lobe of the cap 81. FIG. 8D shows the cap 81 with the fastener piercing the upper or superior part of the superior articular process and the lobe of the cap is oriented inferiorly to capture the inferior articular process with the lobe of the cap 81. FIG. 8E shows the cap 81 with the fastener piercing the inferior articular process (transfacet) and the lobe of the cap 81 is oriented medially to capture the inferior articular process with the lobe of the cap 81. It is appreciated that any of the implants disclosed herein can be implanted in any of the orientations disclosed in FIGS. 8A-8E, including implants with circular footprints or perimeters.

FIG. 9 shows an isometric view of an implant 91 affixed to a facet joint in a cervical portion of the spine 90 demonstrating that the implants disclosed herein can be used in all portions of the spine as well as in other parts of the body.

Methods of inserting the implants disclosed herein will now be given. These methods may be used with any of the implants including caps 10, 20, 21, 22, 23, 30, 40, and implants 71, 81, 91, 100, 200, 300, 400. A K-wire can be inserted into the portion of the facet joint where the surgeon desires to affix the fastener to the facet joint. In one example, the K-wire can be inserted into the inferior facet joint and oriented such that the fastener will enter into the pedicle of the inferior facet joint.

Figure 10:
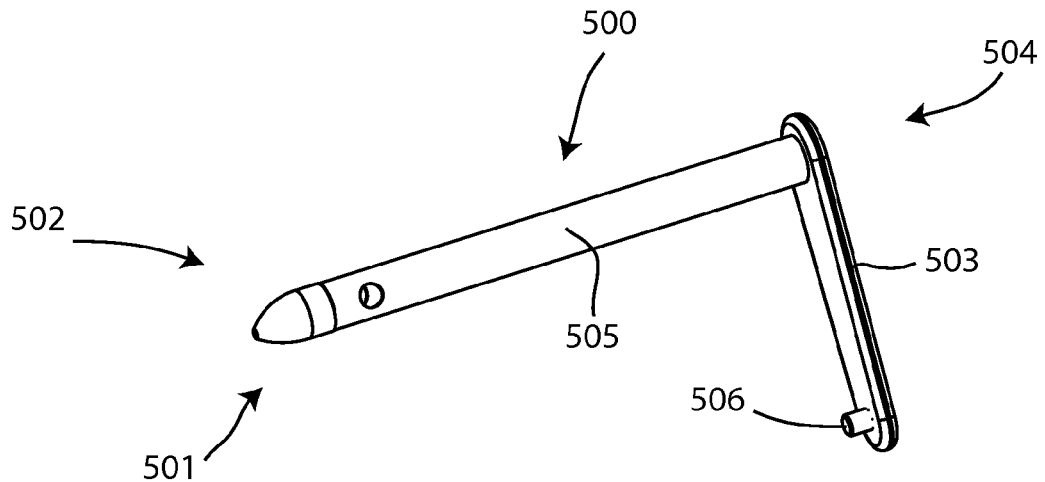
FIG. 10 shows an isometric view of a dilator in accordance with one example of the present disclosure.
Figure 11:
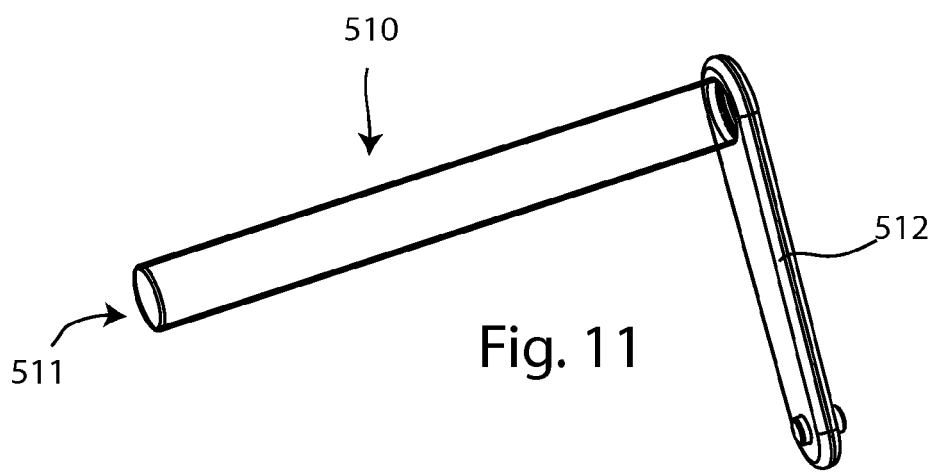
FIG. 11 shows an isometric view of a cannula in accordance with one example of the present disclosure.
Figure 12:
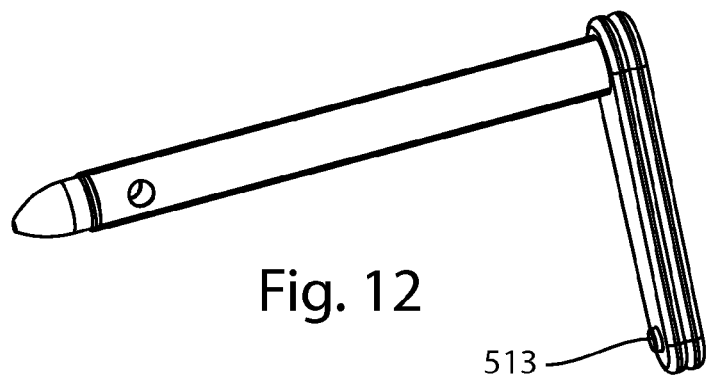
FIG. 12 shows the dilator of FIG. 10 inserted into the cannula of FIG. 11.

Once the K-wire is in the desired location, a dilator 500 and cannula 510 assembly can be threaded over the K-wire and inserted into the soft tissue of the patient to provide sufficient access to the facet joint. FIG. 10 shows an isometric view of a dilator 500 according to one example of the present disclosure. The dilator 500 can have a pointed tip 501 at its distal end 502 and a handle portion 503 at its proximal end 504. The dilator 500 can also have a shaft 505 having a diameter slightly less than the inside diameter of the hollow shaft 511 of a cannula 510 as seen in FIG. 11. The dilator 500 can be inserted into the cannula 510 as shown in FIG. 12, and the handles 503, 512 of the dilator 500 and the cannula 510 can also align with and engage each other via a boss 506 attached to the handle 503 of the dilator 500 and an aperture 513 formed in the handle 512 of the cannula 510.

Figure 13:
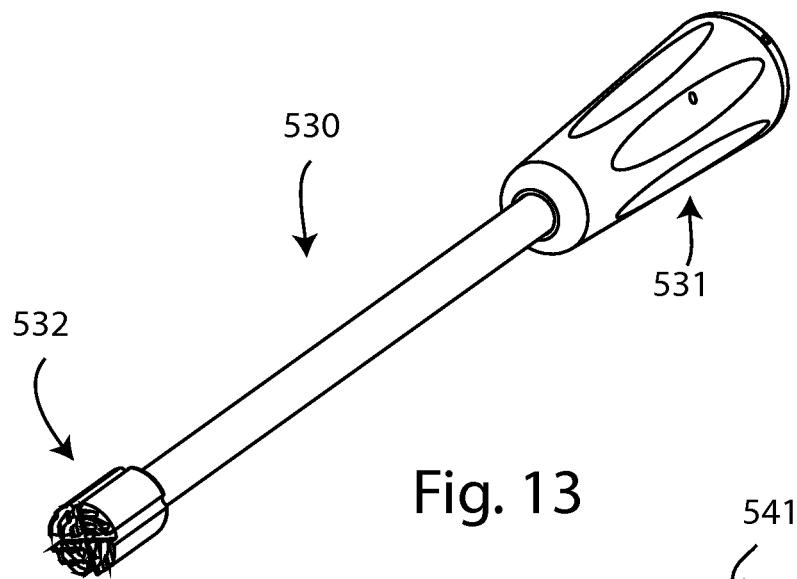
FIG. 13 shows an isometric view of a manual reamer in accordance with one example of the present disclosure.
Figure 14:
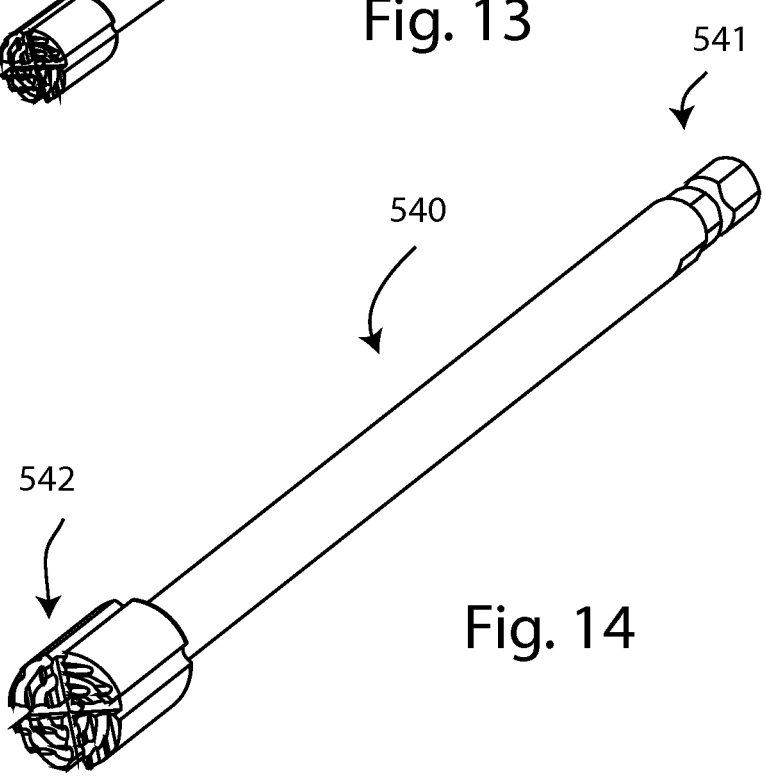
FIG. 14 shows an isometric view of a powered reamer in accordance with another example of the present disclosure.

Once the tissue is dilated, the surgeon can remove the dilator 500 from the cannula 510 thus exposing the facet joint through the cannula for the remainder of the surgery. The surgeon may then ream the bone surface of the facet joint with a suitable reamer 530, 540 to prepare the bone surface for receiving the implant. The reamer 530 shown in FIG. 13 is a manual reamer with a handle 531 and a reamer head 532. The reamer 540 shown in FIG. 14 is a powered reamer with a connection 541 configured to receive a suitable power tool and a reamer head 542.

Figure 15A:
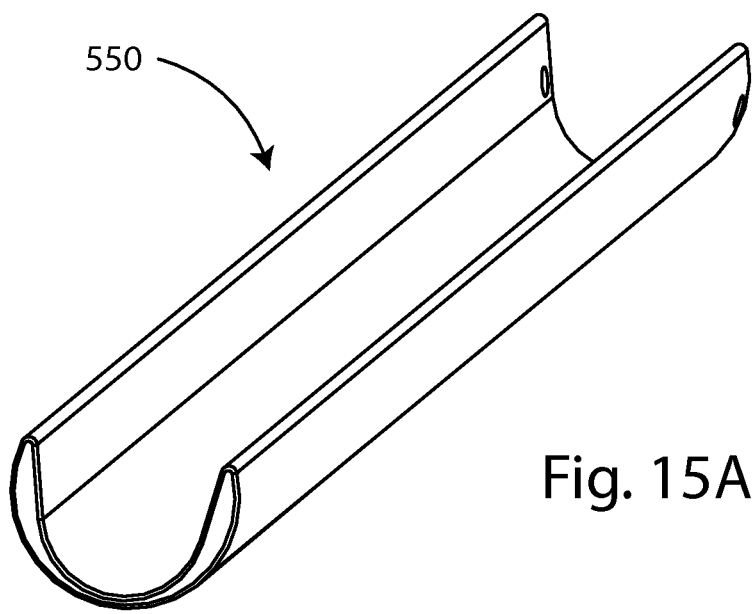
FIG. 15A shows an isometric view of a guide in accordance with one example the present disclosure.
Figure 15B:
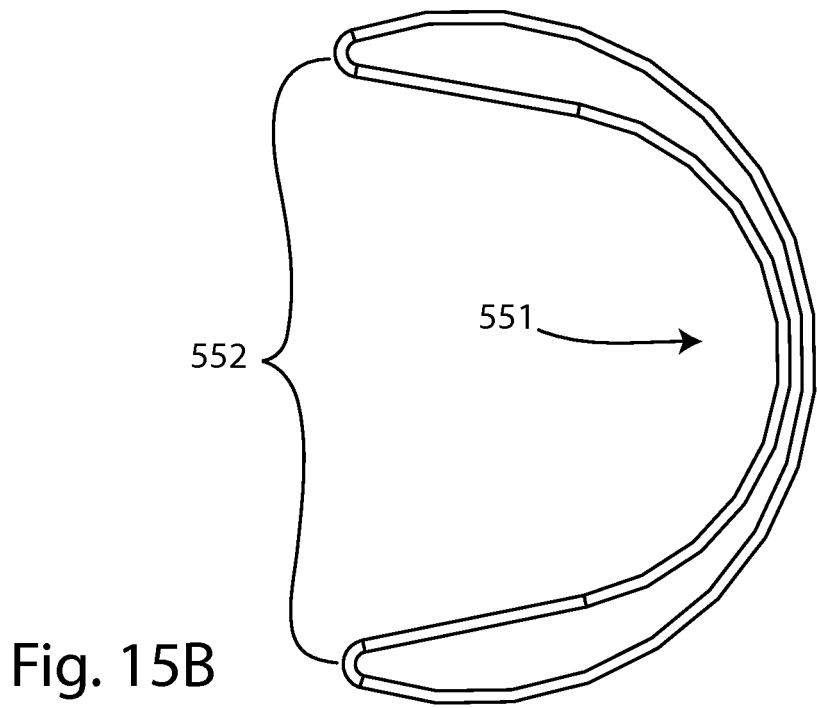
FIG. 15B shows a front view of the guide of FIG. 15A.

Once the implant site is sufficiently prepared to receive the implant, one or more guides can be used to orient and insert a suitable implant, as can be seen in FIGS. 15A-17C. FIGS. 15A-15B illustrate one example of a guide 550 that may be used with an implant 30 shown in FIG. 3. The implant 30 does not have any slots to engage a portion of the guide 550, as other embodiments disclosed herein. Rather, the guide 550 is shaped to receive the smaller second portion of the cap 30 in the smaller inner portion 551 of the guide 550 and the larger first portion of the cap 30 in the larger inner portion 552 of the guide 550, as is shown in the front view of the guide in FIG. 15B. The guide 550 is a semi-tubular or semi-cylindrical member. The outer diameter of the guide 550 may be round to complementarily fit within the cannula 510, but the inner diameter can have a unique cutout profile to accommodate a cap with a variable diameter, such as caps 10, 20, 30, 40. In the example shown, the guide 550 may not be quite a half-pipe as it sweeps close to 245°. Other guide examples may vary in size and shape to accommodate the geometry of other cap embodiments, including caps 10, 20, 21, 22, 23, 40, 102, 202, 302, 402, and 402'. The inner diameters of the cannula 510 and guide 550 match the two different outer diameters of the cap 30; other guides may match the outer diameters of the lobes or perimeters of the other caps. This provides control for proper placement of the cap 30. Thus, the guide 550 is shaped to cooperate with the asymmetrical or eccentric geometry of the cap 30 to guide the cap 30 into place. The guide 550 can be inserted into the cannula 510 and a cap 30 with a suitable fastener attached thereto can be affixed to a suitable driver 580, such as that shown in FIG. 18. The cap 30 can then be inserted into the guide and moved toward the implant site. The shape of the guide 550 in combination with the shape of the implant 30 keeps the cap 30 in the proper orientation as the surgeon slides the cap 30 toward the implant site, and as the fastener is driven into the bone. Caps having a circular base perimeter such as caps 102, 202, 302, 402, and 402' may be implanted with a guide 550 having a circular inner diameter; alternately the guide 550 may not be used and the cap may be implanted directly through the cannula 510.

The driver 580 can have a hexagonal tip 581 configured to interact with a hexagonal aperture 52 as seen in FIG. 5A. The hexagonal aperture 52 can also be chamfered to help the driver 580 stay engaged with the fastener 50.

In one method of implantation, the cap 30 may be placed first, allowing the teeth to capture bone surfaces on both sides of the joint, followed by placement of the screw 30 to provide compression and stability. As the fastener head 51 engages in spherical capsule 12, the teeth 14 are driven into the bone; the beveled surfaces 15 of the teeth promote compression across the facet joint.

Figure 16:
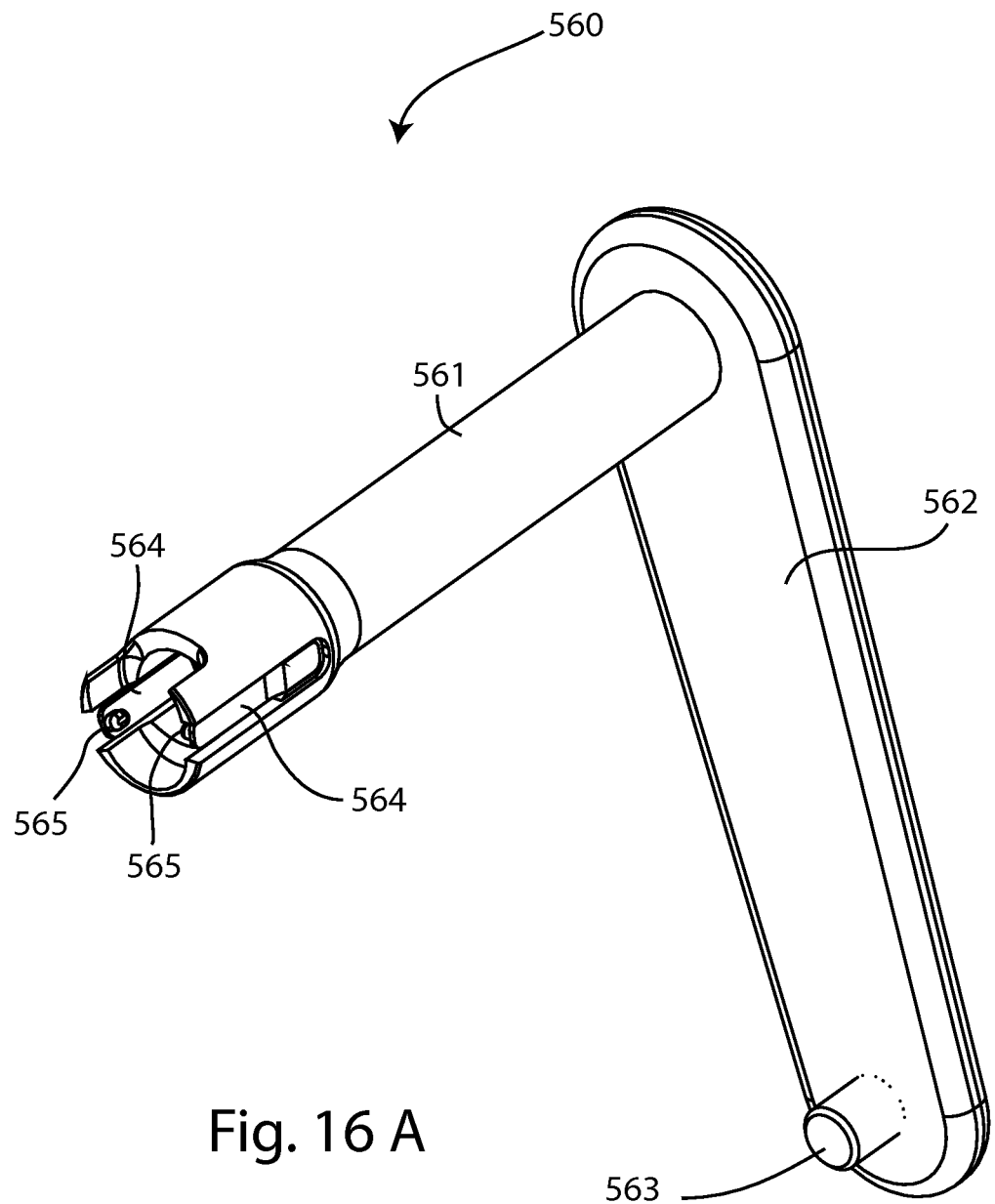
FIG. 16A shows an isometric view of a guide in accordance with another example the present disclosure.
FIG. 16B shows an isometric view of the guide of FIG. 16A with a cap inserted into the guide.
FIG. 16C shows an isometric view of the guide of FIG. 16A with a cap and fastener assembly inserted into the guide.
Figure 16B:
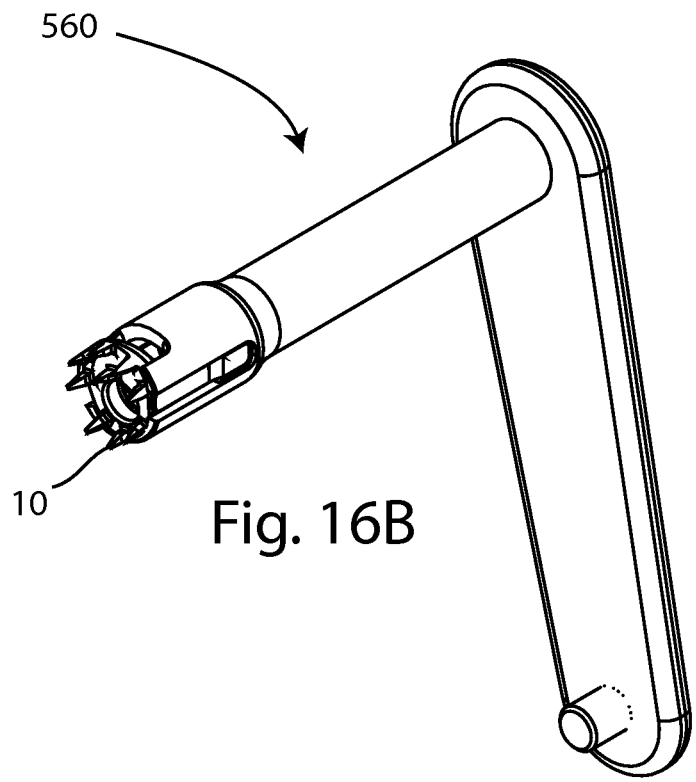
Figure 16C:
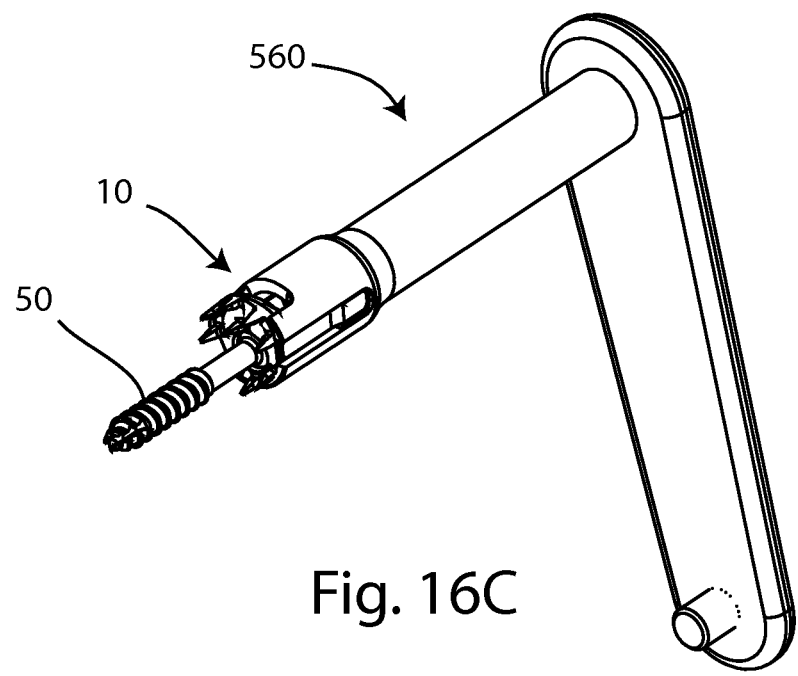

FIGS. 16A-16C show an alternative example of a guide for use with other implants described herein. The guide 560 can have a shaft 561 and a handle 562 with a boss attached to the handle 562. The shaft 561 can be hollow and can include one or more retaining members 564 engaged with the distal end of the hollow shaft 561. Moreover, the retaining members 564 can include boss members 565 sized and shaped to engage suitably shaped recessed slots 18 formed in the cap 10. In other examples, the cap 10 may include other features to cooperate with the one or more retaining members 564, such as recesses, dimples, or grooves. The boss members 565 may be oriented to be offset from each other at the distal end of guide 560 in order to match the offset or eccentric shape of the slots 18 in the cap 10. Guide 560 may also be used to implant devices 100, 200, 300, and 400; boss members 565 can be received in the connection features of caps 102, 202, 302, 402 to guide the caps toward the implantation site and hold the implant while the fastener 104, 204, 304, 404 is engaged in the bone.

Figure 17A:
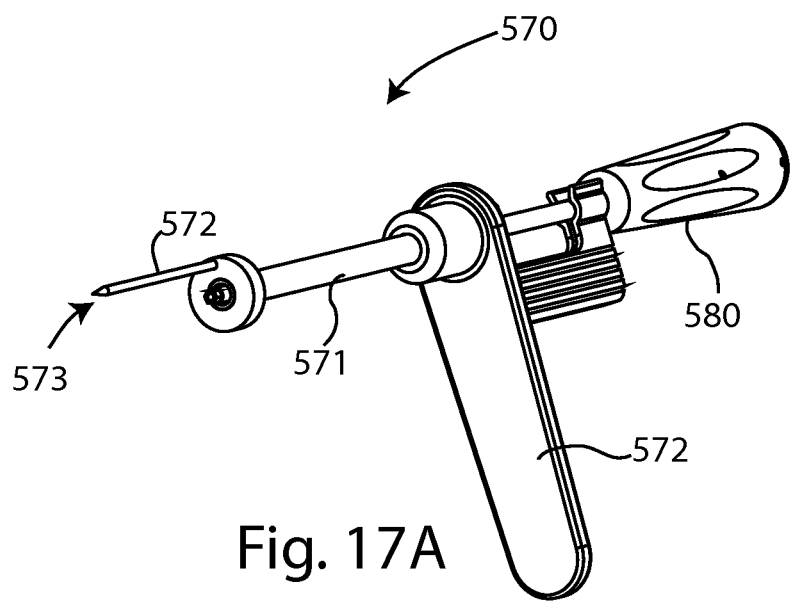
FIG. 17A shows an isometric view of a guide in accordance with another example the present disclosure.
Figure 17B:
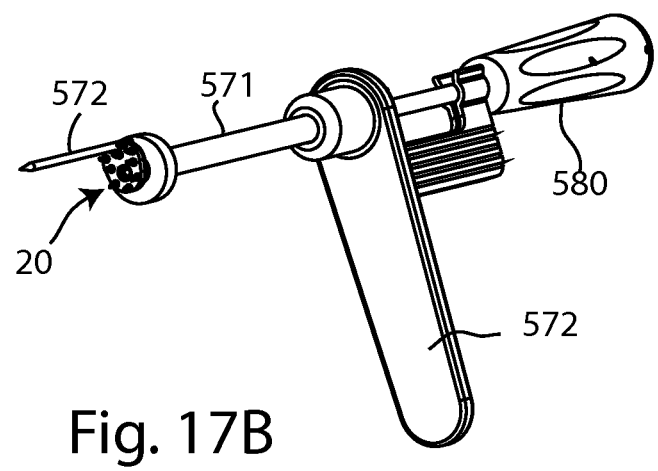
FIG. 17B shows an isometric view of the guide of FIG. 17A with a cap inserted into the guide.
Figure 17C:
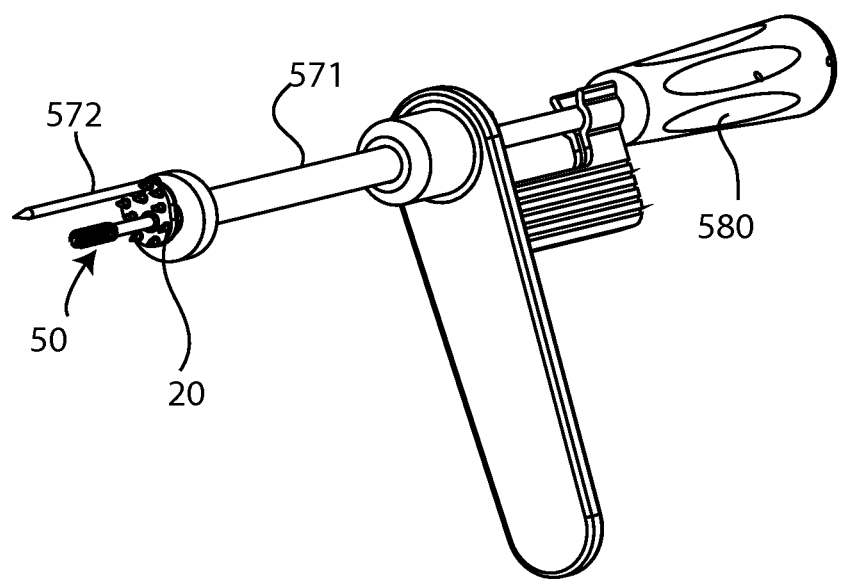
FIG. 17 C shows an isometric view of the guide of FIG. 17A with a cap and fastener assembly inserted into the guide.
Figure 18:
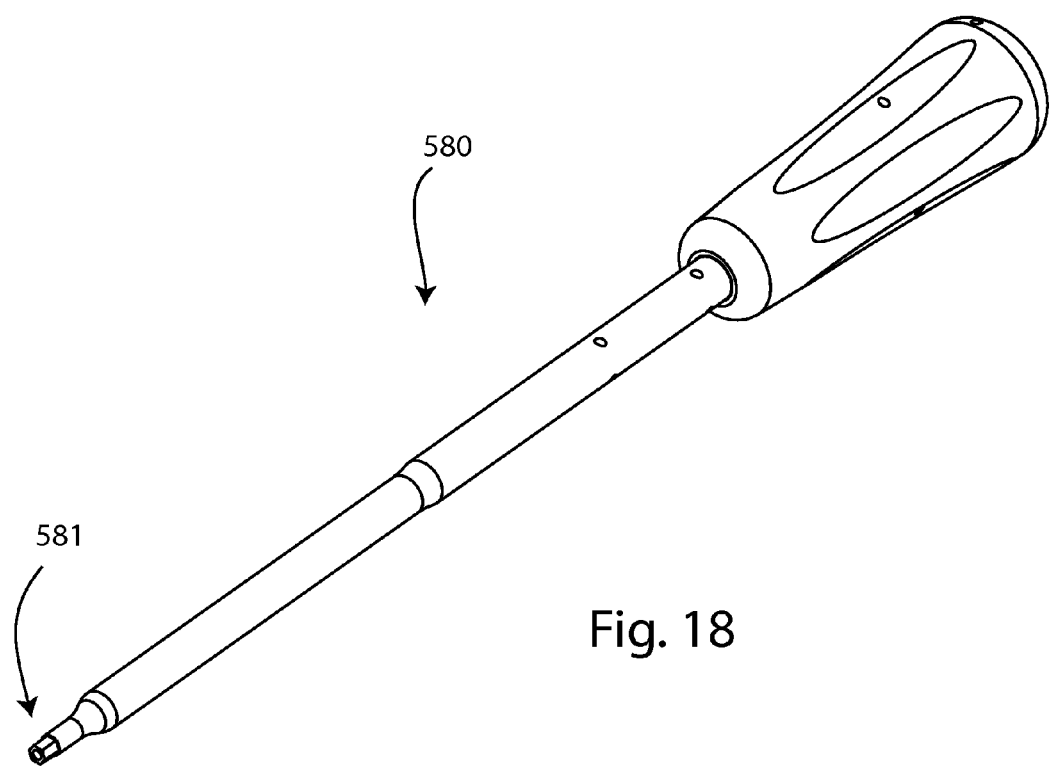
FIG. 18 shows an isometric view of a fastener driver in accordance with one example of the present disclosure.

FIG. 17A-17C show yet another example of a guide for use with implants disclosed herein. The guide 570 can have a hollow shaft 571 and a guide pin 572. The guide pin 572 may be offset from a central longitudinal axis of the guide 570. The guide pin 572 cooperates with the slot 26 on the cap 20 to guide the cap 20 along a selected path into proper alignment with the joint. Guide pin 572 may also include a tip 573 which can act as a probe to aid in referencing the joint space. FIG. 17B shows the guide 570 with a cap 20 engaged with the guide 570 via a driver 580 and the guide pin 572. FIG. 17C shows the guide 570 engaged with fastener 50 and cap 20 with the driver 580 pushing the cap 20 and fastener 50 in the distal direction along the guide pin 572. FIG. 18 shows an isometric view of the driver 580 with a hexagonal tip 581. In other examples, the hexagonal tip 581 may be replaced with another shaped drive feature for connection with a suitable fastener. Any of the other cap embodiments disclosed herein may include slots 26 to allow use of guide 570 during an implantation procedure.

All of the above guides can be used to orient, steer, and insert the implant to the desired location at the implant site where the driver 580 can then be used to apply a torsional rotation force to the fastener 50 to fasten the implant to the joint to stabilize the joint. Once the implant is in the proper location, the surgeon can remove the guide, the driver 580, the cannula 510, and the K-wire and then close the incision site.

Figures 19A, 19B:
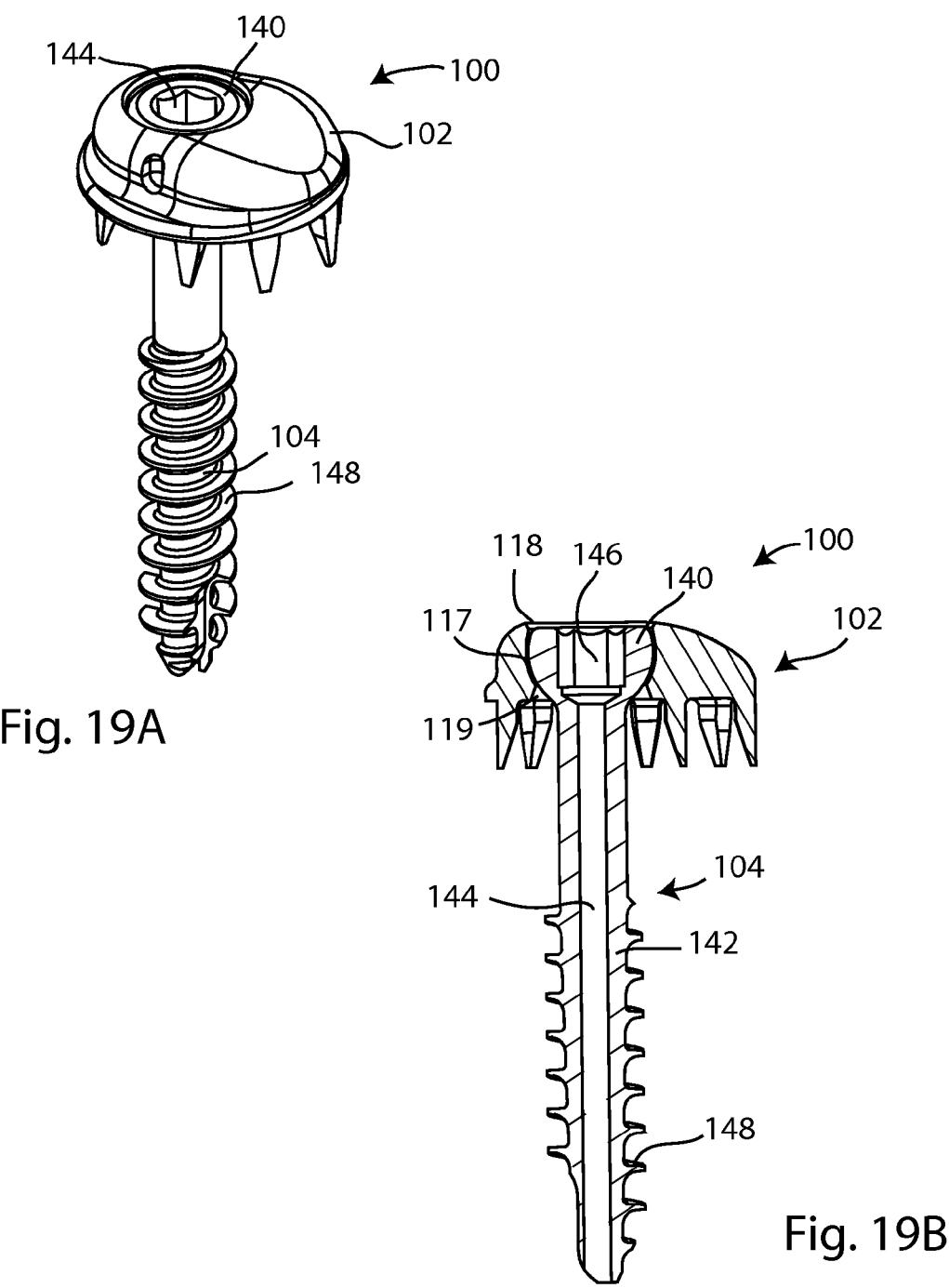
FIG. 19A is an isometric view of a facet fixation device having a facet fixation cap with a circular footprint and a screw.
FIG. 19B is a side cross-sectional view of the facet fixation device of FIG. 19A.

Referring to FIGS. 19A and 19B, another embodiment of a facet fixation device is shown. Device 100 includes a cap 102 and a fastener which in this embodiment is a screw 104. Device 100 and the other facet fixation devices herein may be referred to as an implant. When implanted, screw 104 may extend through cap 102 and through a facet joint, fastening cap 102 to the facet joint and stabilizing the joint. The cap 102 may span the joint, with a portion of the cap affixed to the inferior articular process of a facet joint, and another portion of the cap affixed to the superior articular process of the facet joint. The width of the cap 102 provides increased load bearing area for the screw 104.

Referring to FIGS. 20A, 20B, 21A and 21B, cap 102 includes a first side 110 and a second side 112, which may be superior and inferior sides, respectively. The first side 110 may be smoothly rounded to provide a low and minimally obtrusive device profile. The second side 112 includes an attachment surface 114. In the embodiment shown, attachment surface 114 is circular, and planar, although in other embodiments the attachment surface may be non-planar. An aperture 116 extends through the cap 102 between the first side 110 and the second side 112. A cap axis 103 is centrally located relative to the aperture 116. The aperture 116 is also circular, although in other embodiments the aperture 116 may take another shape. The aperture 116 is offset, or eccentrically positioned relative to the geometric center of the cap 102 and the outer circular footprint of the cap. Aperture 116 is circumscribed by an aperture wall 117, which is spherically concave or cup-shaped to receive the head of screw 104. In other embodiments, the aperture wall may be flat or conically concave. Toward the first side 110, aperture wall 117 widens at a first flared end 118 and toward the second side 112, aperture wall 117 widens at a second flared end 119, best seen in FIG. 19B. In another embodiment, cap 102 may include a second aperture 41 which is a fenestration to provide a graft pocket for material such as demineralized bone material, graft material, bone chips or bone growth promoters.

Figure 20A:
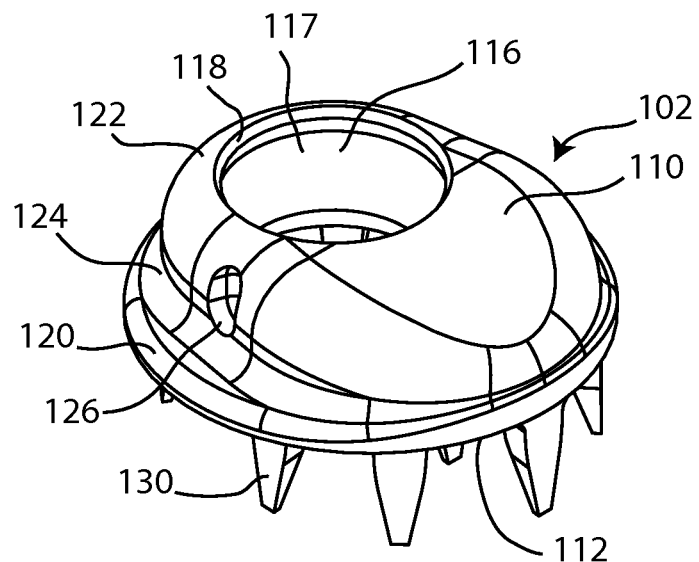
FIG. 20A is an isometric view of an embodiment of the facet fixation cap of FIG. 19A.
Figure 20B:
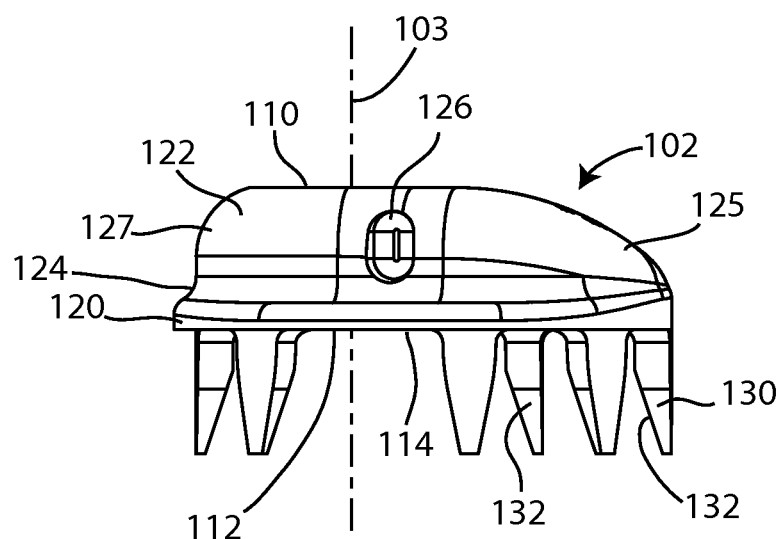
FIG. 20B is a side view of the cap of FIG. 20A.
Figure 21A:
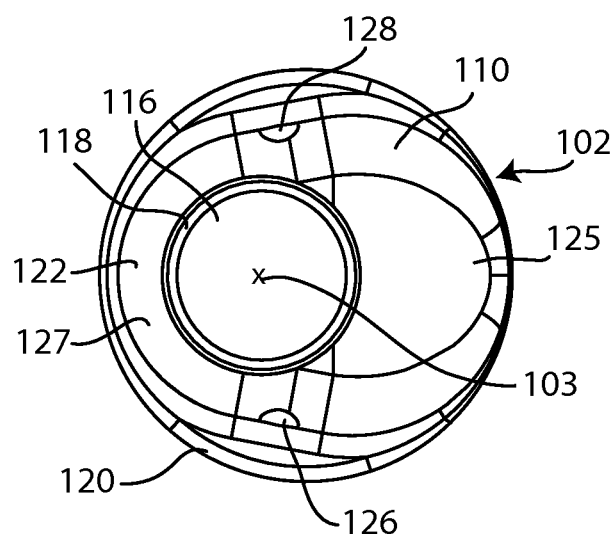
FIG. 21A is a superior view of the cap of FIG. 20A.
Figure 21B:
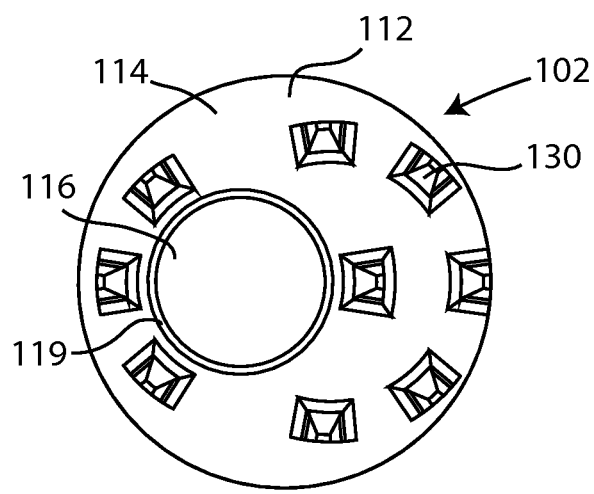
FIG. 21B is an inferior view of the cap of FIG. 20A.
Figure 22A:
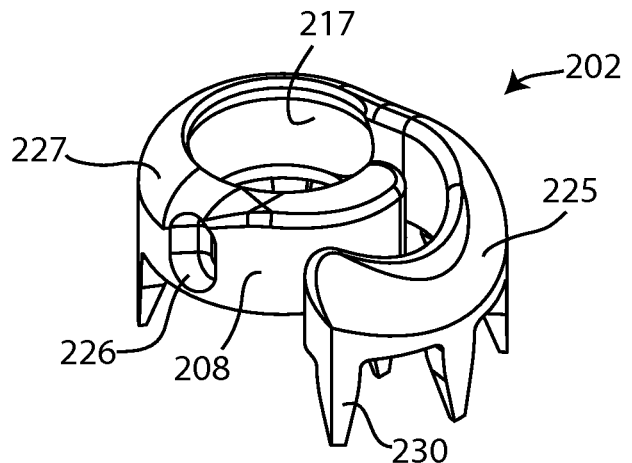
FIG. 22A is an isometric view of an embodiment of a facet fixation cap having a spiral footprint.
Figure 22B:
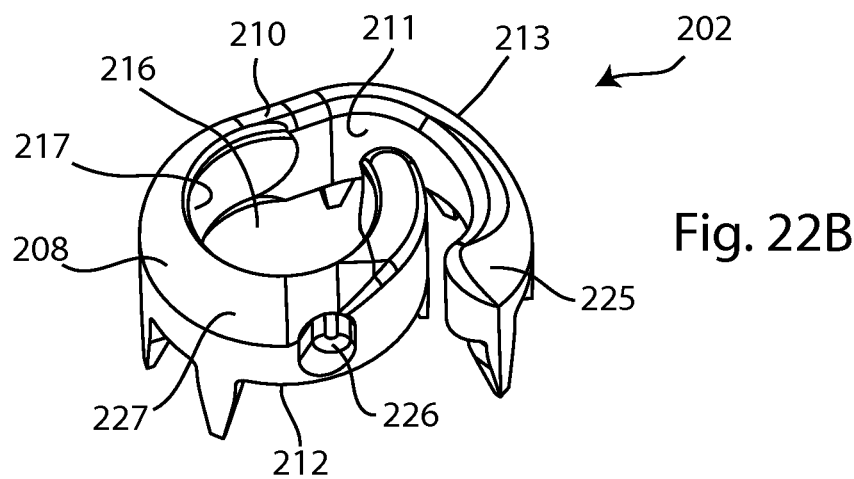
FIG. 22B is another isometric view of the cap of FIG. 22A.
Figure 22C:
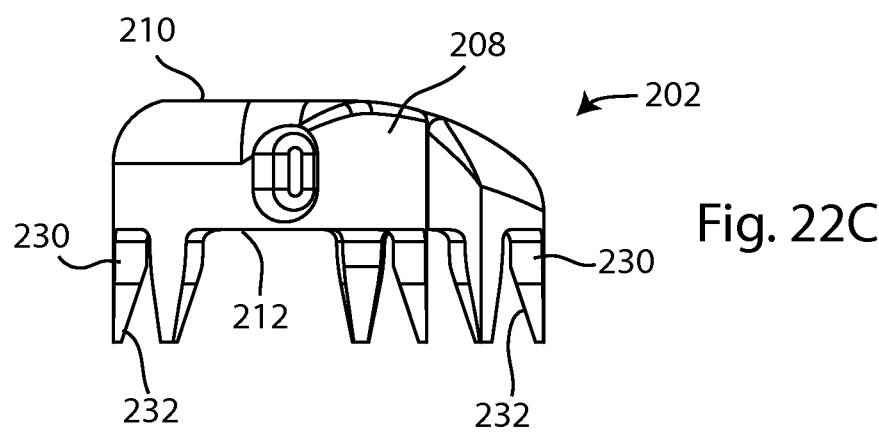
FIG. 22C is a side view of the cap of FIG. 22A.
Figure 23A:
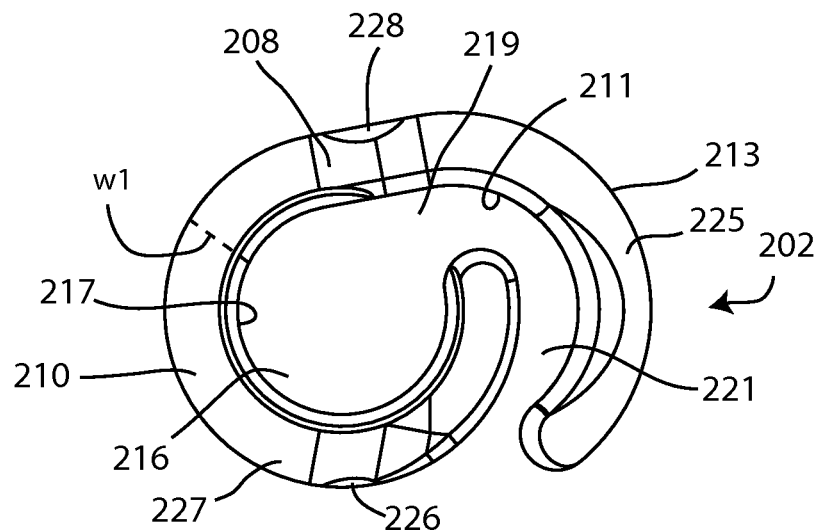
FIG. 23A is a superior view of the cap of FIG. 22A.
Figure 23B:
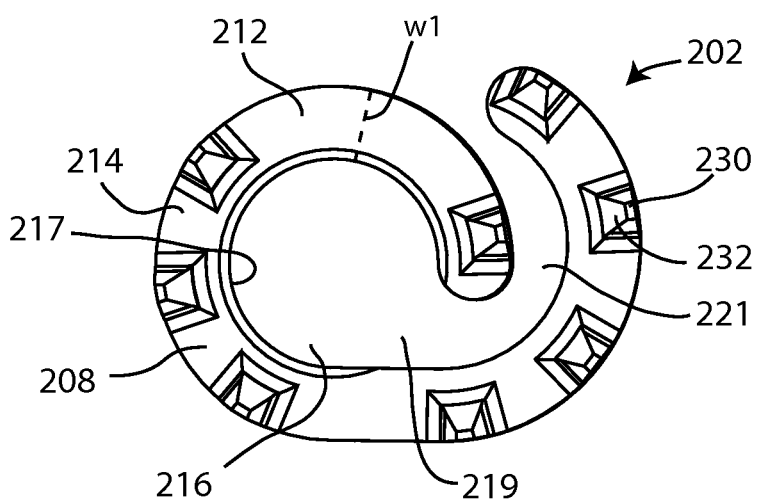
FIG. 23B is an inferior view of the cap of FIG. 22A.

The cap 102 further includes a base portion 120 and a raised portion 122. The base portion 120 is shaped as a circular flange with a circular perimeter, and the raised portion 122 projects superiorly from the base portion 120. In the context of this disclosure, a perimeter is a line bounding a cap portion at its largest extent, the line bounding a plane perpendicular to the cap axis. While the base portion 120 is circular with a circular perimeter, the raised portion 122 is not radially symmetrical and has a non-circular, eccentric perimeter, and in the embodiment shown is ovoid, having a wider first end 125 and a relatively narrower second end 127. The first and second ends 125, 127 may be lobes of the raised portion 120; the widths of the lobes 125, 127 are measured in a plane perpendicular to the cap axis 103. The second end or lobe 127 encompasses the aperture 116. Toward its juncture with the base portion 120, the raised portion 122 includes a flared section 124 which extends around at least a portion of the raised portion 122. The flared section 124 provides a concavely curved transition between the base portion 120 and the raised portion 122. As best seen in FIGS. 20A and 21A, the circular base portion 120 projects radially outward beyond the raised portion 122 in every direction normal to axis 103. This shape allows the base portion to provide a maximum footprint area for attachment to the facet joint and compression across the joint, while the raised portion is reduced in size from the base portion, providing a minimally obtrusive device profile.

At least one connection feature which may be a recess is present on the cap. Cap 102 includes two connection features 126, 128 which are recessed into the raised portion 120, and provide a location for an instrument to grasp the cap 102. Connection features 126, 128 may cooperate with retaining members 564 of instrument 560 allowing instrument 560 to guide placement of cap 100 in an implantation procedure. In alternate embodiments, the connection features may be formed as slots in communication with the aperture, or as protruding bosses or tabs. The flared section 124 may also provide a recessed surface for instrument connection. In other embodiments, the cap 102 may include one or more slots 24 for connection to a guiding or implantation instrument.

The attachment surface 114 includes a plurality of teeth 130 projecting inferiorly from the cap. The teeth 130 may vary in number and in distribution. Each tooth 130 may include at least one bevel 132. The bevels 132 may be oriented, or face interiorly toward, the center of the attachment surface 114. The positioning of the beveled teeth may provide compression across the joint as the cap 102 is affixed to the joint, as the beveled tooth surfaces on teeth on one side of the joint may oppose, or face, beveled tooth surfaces on teeth on the opposite side of the joint. Methods of implantation described above for cap 10 and fastener 50 also apply to devices 100, 200, 300, and 400.

Referring to FIGS. 19A and 19B, cap 102 is shown with screw 104. Screw 104 includes a head portion 140, a shaft portion 142, and is cannulated with a bore 144 extending the length of the screw. The head 140 includes a connection feature 146 which may be a hex connection or other type of connection which permits a driver to turn the screw 104. Screw 104 may be polyaxially adjustable relative to cap 102, with head 140 rotatable polyaxially within aperture wall 117. The second flared end 119 may allow space for the polyaxial tilting of the screw relative to the longitudinal axis of the aperture 116 and cap axis 103. Shaft portion 142 is at least partially threaded, with threads 148 occupying a portion of the shaft. It is appreciated that in other embodiments of device 100 and the other facet fixation devices herein, the screw 104 may be replaced with another type of fastener. For example, a rivet, brad, nail, bolt, post, peg, staple, anchor, line, flexible member, cable, wire or another type of fastener known in the art may be used to provide fixation of the cap across a facet joint. Screw 104 or other fastener may lock to the cap to prevent backout of the screw 104 or backout of the cap 102.

Referring to FIGS. 22A, 22B, 22C, 23A and 23B, an embodiment of a facet fixation cap having a spiral shape is shown. Cap 202 is formed as a continuous snake-like shape, having a first end or lobe 225 which winds around and partially overlaps a second end or lobe 227. The spiral may be asymmetrically shaped, with an overall length of the cap greater than an overall width. Cap 202 includes a cap body 208 having a first side 210 opposite a second side 212; the cap also has an interior wall 211 opposite an exterior wall 213. The interior 211 and exterior 213 walls are generally perpendicular to the second side 212. As seen best in FIGS. 23A and 23B, the thickness, or width w1, of the cap body 208 between the interior wall 211 and the exterior wall 213 is constant throughout the cap body; in other embodiments the width of the cap body may vary at different locations. Exterior wall 213 may be smoothly rounded to provide a low unobtrusive profile when the cap 202 is implanted.

Cap 202 further includes an attachment surface 214 having a plurality of teeth 230 with bevels 232. As with cap 102, the positioning of the teeth and bevels promotes compression across the facet joint when the cap 202 is implanted with some teeth on one side of the joint, and the remaining teeth on the other side of the joint. An aperture 216 having a surrounding aperture wall 217 is formed in the second lobe 227; in the embodiment the aperture 216 is not entirely closed off but a first gap 219 is formed in the aperture wall 217. First and second connection features 226, 228 are formed as recesses in cap body 208, on the exterior wall 213. It is appreciated that one or more connection features may be formed on any part of the cap body 208 in any location. In alternate embodiments, the connection features may be formed as slots in communication with the aperture, or as protruding bosses or tabs. In other embodiments, the cap 202 may include one or more slots 24 for connection to a guiding or implantation instrument. A second gap is formed between the first lobe 225 and the second lobe 227. The first and second gaps 219, 221 may be referred to as fenestrations, and provide space for insertion of bone graft material.

Figure 24A:
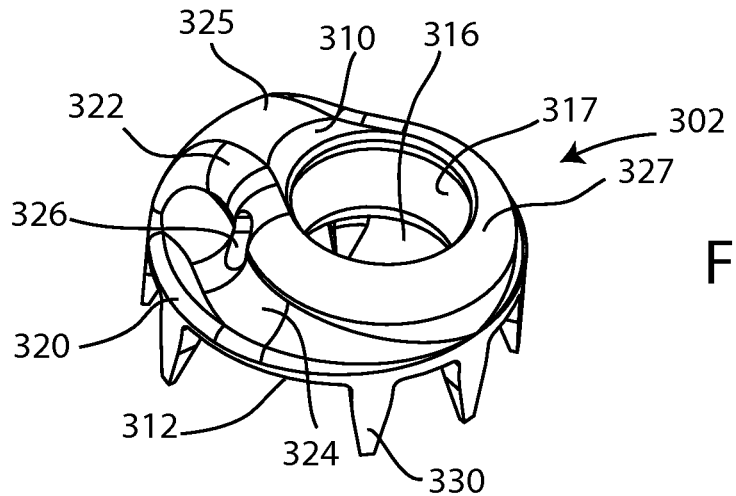
FIG. 24A is an isometric view of another embodiment of a facet fixation cap having a circular footprint.
Figure 24B:
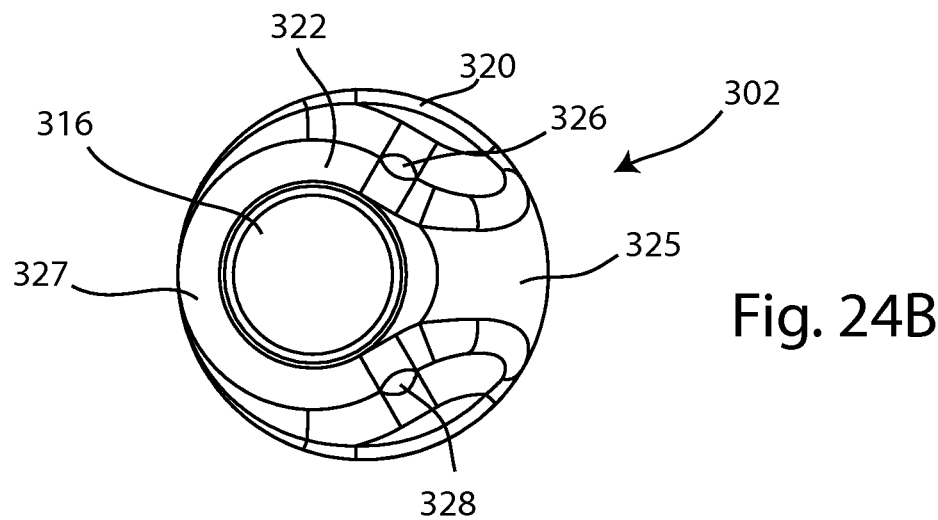
FIG. 24B is superior view of the cap of FIG. 24A.
Figure 24C:
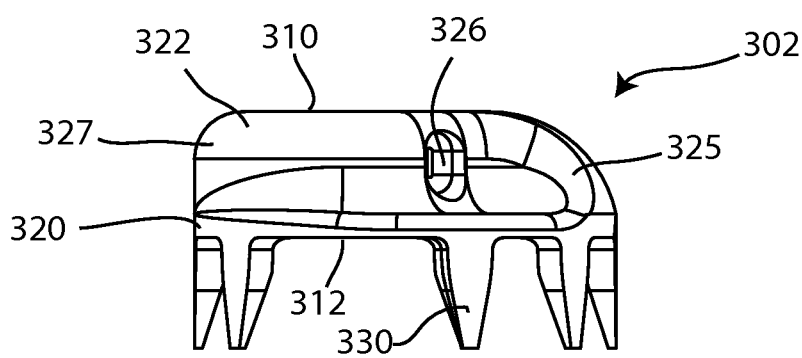
FIG. 24C is a side view of the cap of FIG. 24A.

Referring to FIGS. 24A, 24B, and 24C, another embodiment of a facet fixation device is shown. Like device 100, a facet fixation cap 302 has a circular footprint. Cap 302 shares many of the characteristics of cap 102, which are numbered similarly, including a first side 310, second side 312, aperture 316, aperture wall 317, attachment surface 314, base portion 320, raised portion 322, flared section 324, beveled teeth 330, and connection features 326, 328, among others. Similar features shown and described for device 102 can be assumed to also apply to cap 302. While the base portion 320 is circular, the raised portion 322 is not radially symmetrical and has a non-circular, eccentric perimeter. The shape of the raised portion 322 differs from the shape of the raised portion 122 of cap 102 in that the relative sizes of the lobes of the raised portion are reversed. A second end, or lobe 327, which encompasses aperture 316, is wider than a first end, or lobe 325. Raised portion 322 has a non-circular, eccentric perimeter, while base portion 320 has a circular perimeter. In alternate embodiments, the connection features may be formed as slots in communication with the aperture, or as protruding bosses or tabs. In other embodiments, cap 302 may include one or more slots 24 for connection to a guiding or implantation instrument. In alternate embodiments, cap 302 may include a second aperture 41 which is a fenestration to provide a graft pocket for material such as demineralized bone material, graft material, bone chips or bone growth promoters.

Figure 25A:
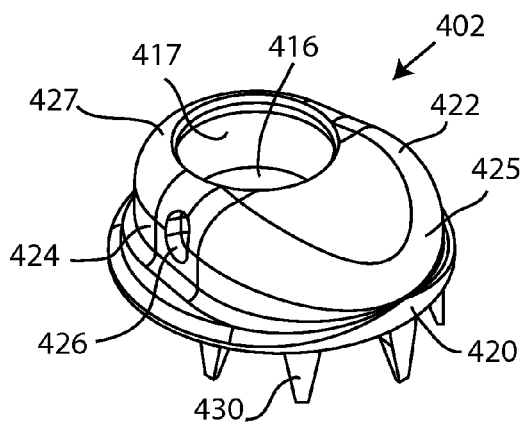
FIG. 25A is an isometric view of another embodiment of a facet fixation cap having a circular footprint.
Figure 25B:
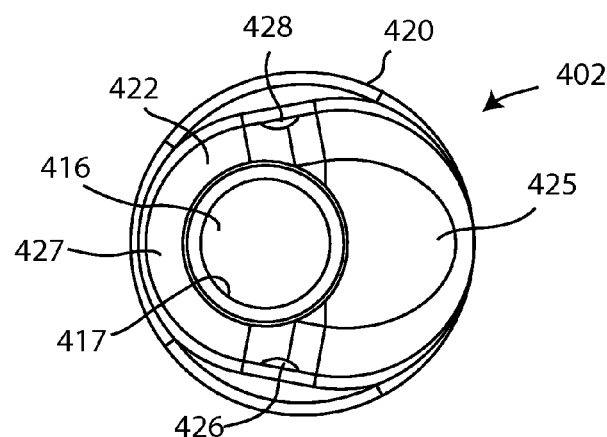
FIG. 25B is a superior view of the cap of FIG. 25A.
Figure 25C:
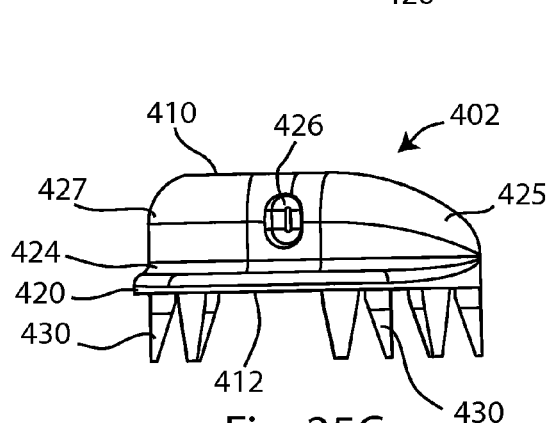
FIG. 25C is a side view of the cap of FIG. 25A.

Referring to FIGS. 25A, 25B, and 25C yet another embodiment of a facet fixation device is shown. Like caps 102 and 302, a facet fixation cap 402 has a circular footprint. Cap 402 shares many of the characteristics of cap 102, which are numbered similarly, including a first side 410, second side 412, aperture 416, aperture wall 417, attachment surface 414, base portion 420, raised portion 422, flared section 424, beveled teeth 430, first and second ends 425, 427, and connection features 426, 428, among others. Similar features shown and described for device 102 can be assumed to also apply to cap 402. The shape of the raised portion 422 differs from the shape of the raised portion 122 of cap 102 in that the raised portion 422 is wider overall, for example between the connection features, compared to raised portion 122 of cap 102. Raised portion 422 of cap 402 overlays more of the base portion 420 than does raised portion 122 of base portion 120 of cap 102; portion 422 may be described as wider or beefier than raised portion 122. Raised portion 422 has a non-circular eccentric perimeter, while base portion 420 has a circular perimeter. A flared section 424 of cap 402 may be less dramatically curved than the flared section 124 of cap 102. In alternate embodiments, the connection features may be formed as slots in communication with the aperture, or as protruding bosses or tabs. In other embodiments, cap 402 may include one or more slots 24 for connection to a guiding or implantation instrument. In alternate embodiments, cap 402 may include a second aperture 41 which is a fenestration to provide a graft pocket for material such as demineralized bone material, graft material, bone chips or bone growth promoters.

Figure 25D:
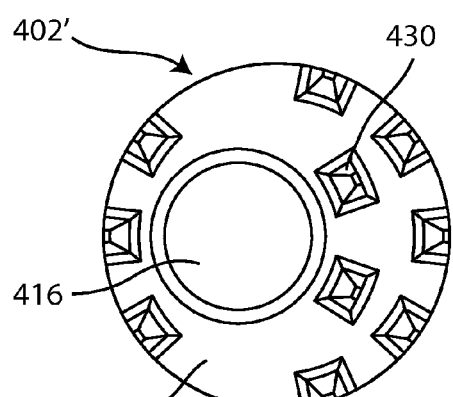
FIG. 25D is an inferior view of an alternative embodiment of the cap of FIG. 25A.

Referring to FIG. 25D, cap 402' is an alternative embodiment of cap 402. Cap 402' shares many of the same features as cap 402; however the number and pattern of teeth 430 projecting from attachment surface 414 differs. Cap 402' has two teeth 430 on the second end 425 between an outer row of teeth and the aperture 416, creating an outer perimeter of teeth and an inner row of teeth. In comparison, cap 402 has only one tooth 430 between an outer row and the aperture. It is appreciated that in any of the embodiments disclosed herein, the number and pattern of teeth may vary; teeth may be distributed in rows, groups, or singly; randomly or regularly; symmetrically or asymmetrically.

Figure 26:
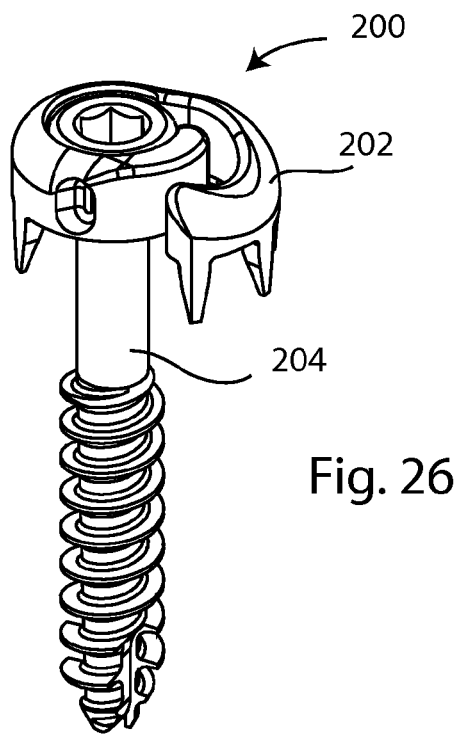
FIG. 26 is an isometric view of a facet fixation device including the cap of FIG. 22A and a screw.

Referring to FIG. 26, a facet fixation device 200 includes cap 202 and screw 204. Screw 204 may be the same as screw 104 and as such will not be further described. Screw 204 may be polyaxially adjustable relative to cap 202. The discontinuous spiral shape of cap 202 may allow some conforming of cap 202 to the targeted joint members when cap 202 is implanted. For example, the attachment surface 214 on lobe 225 may not remain coplanar with attachment surface 214 on lobe 227 as device 200 is implanted; some relative movement may occur between lobe 225 and lobe 227.

Figure 27:
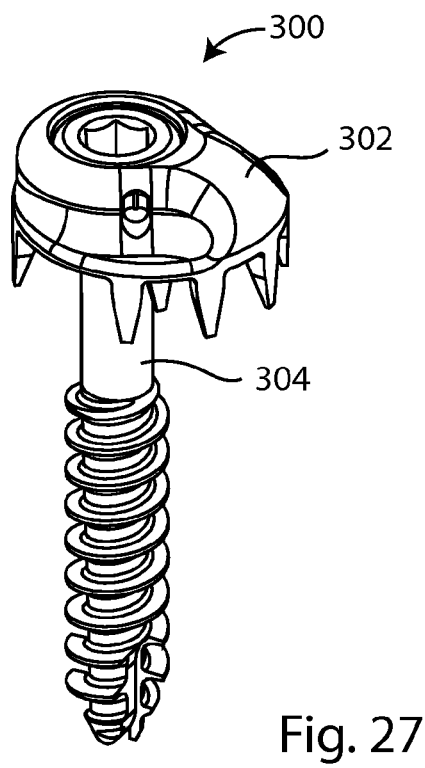
FIG. 27 is an isometric view of a facet fixation device including the cap of FIG. 24A and a screw.

Referring to FIG. 27, a facet fixation device 300 includes cap 302 and screw 304. Screw 304 may be the same as screw 104 and as such will not be further described. Screw 304 may be polyaxially adjustable relative to cap 302.

Figure 28:
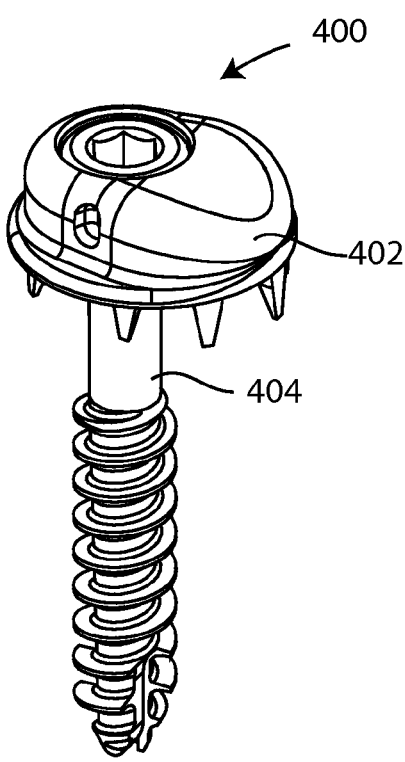
FIG. 28 is an isometric view of a facet fixation device including the cap of FIG. 25A and a screw.

Referring to FIG. 28, a facet fixation device 400 includes cap 402 and screw 404. Screw 404 may be the same as screw 104 and as such will not be further described. Screw 404 may be polyaxially adjustable relative to cap 402.

It should be understood that the present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, a connection feature, slot, fenestration and/or tooth configuration from one or more cap examples may be found on the other caps disclosed herein. Similarly, manufacturing, assembly or implantation methods described for one cap may be used in the manufacture, assembly or implantation of the other caps disclosed herein. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A device for facet joint fixation, the device comprising:
   a fastener; and
   a cap, the cap including:
   a base portion having a center and a circular perimeter symmetrically arranged about the center of the base portion, an aperture extending through the base portion along a cap axis, wherein the cap axis is centrally located relative to the aperture, the aperture is offset from the center of the base portion, the aperture is shaped to receive the fastener to allow the fastener to fasten the cap to a facet joint to stabilize the facet joint, and the fastener is polyaxially adjustable within the aperture;
   a raised portion protruding from the base portion along a first direction of the cap axis, the raised portion having a non-circular perimeter, wherein the raised portion is reduced in size from the base portion such that the raised portion's noncircular perimeter does not extend beyond the base portion's circular perimeter in a horizontal plane perpendicular to the cap axis, the raised portion including a first lobe and a second lobe opposite the first lobe in the horizontal plane perpendicular to the cap axis along a second direction of the raised portion transverse the first direction of the cap axis, the aperture extending through the second lobe of the raised portion, a sidewall raised along the first direction connecting the first lobe with the second lobe;
   wherein the first lobe is wider than the second lobe in the horizontal plane perpendicular to the cap axis and along a third direction of the raised portion transverse to the first direction and the second direction of the raised portion; and
   wherein the base portion includes an attachment surface opposite the raised portion, a plurality of teeth projecting from the attachment surface, each tooth having at least one beveled surface, wherein the teeth are arranged on the attachment surface so that at least two beveled surfaces face one another on opposing sides of the aperture.

2. The device of claim 1, wherein the fastener is a screw, wherein the screw is polyaxially adjustable relative to the cap.

3. The device of claim 1, wherein the plurality of teeth are arranged on the attachment surface so that the beveled surfaces are oriented inwardly from the base portion perimeter.

4. The device of claim 1, wherein the aperture is circumscribed by an aperture wall, wherein the aperture wall is spherically concave.

5. The device of claim 4, wherein the aperture wall has a first end intersecting the raised portion and a second end intersecting the attachment surface, wherein the aperture wall widens relative to the cap axis at one of the first and second ends.

6. The device of claim 1, wherein the raised portion includes a pair of connection features shaped to receive a guiding instrument.

7. The device of claim 6, wherein the connection features are recesses, and wherein the connection features are on opposite sides of the aperture.

8. The device of claim 1, wherein the perimeter of the raised portion is eccentric.

9. The device of claim 8, wherein the raised portion is ovoid shaped.

10. The device of claim 9, wherein the cap further includes a flared section at the juncture of the base portion and the raised portion, the flared section providing a curved transition between the base portion and the raised portion.

11. The device of claim 10, wherein the cap further includes a fenestration, the fenestration providing a pocket for graft material.

12. The device of claim 10, wherein the attachment surface is planar, and wherein the raised portion is smoothly rounded to provide a low and minimally obtrusive device profile.

13. The device of claim 1, wherein a first tooth of the plurality of teeth is positioned adjacent the base portion perimeter, and wherein a second tooth of the plurality of teeth is positioned interior to the first tooth, between the first tooth and the aperture.

* * * * *